(12) United States Patent
Boerjan et al.

(10) Patent No.: US 9,834,776 B2
(45) Date of Patent: Dec. 5, 2017

(54) METHOD FOR MODIFYING LIGNIN BIOSYNTHESIS IN PLANTS

(71) Applicants: University of Dundee, Dundee (GB); VIB VZW, Ghent (BE); Universiteit Gent, Ghent (BE)

(72) Inventors: Wout Antoon Corneel Boerjan, Ghent (BE); Claire Halpin, Invergowrie (GB); Gordon Grant Simpson, Invergowrie (GB); Ruben Vanholme, Destelbergen (BE)

(73) Assignees: University of Dundee, Dundee (GB); VIB VZW, Ghent (BE); Universiteit Gent, Ghent (BE)

( * ) Notice: Subject to any disclaimer, the term of this patent is extended or adjusted under 35 U.S.C. 154(b) by 0 days.

(21) Appl. No.: 14/399,901

(22) PCT Filed: May 9, 2013

(86) PCT No.: PCT/GB2013/051206
§ 371 (c)(1),
(2) Date: Nov. 7, 2014

(87) PCT Pub. No.: WO2013/167902
PCT Pub. Date: Nov. 14, 2013

(65) Prior Publication Data
US 2015/0176016 A1    Jun. 25, 2015

(30) Foreign Application Priority Data
May 9, 2012 (GB) .................................. 1208105.5

(51) Int. Cl.
C12N 15/82    (2006.01)
C12N 9/16    (2006.01)
C12P 7/10    (2006.01)
C12P 19/00    (2006.01)

(52) U.S. Cl.
CPC .......... *C12N 15/8216* (2013.01); *C12N 9/16* (2013.01); *C12N 15/8255* (2013.01); *C12P 7/10* (2013.01); *C12P 19/00* (2013.01); *Y02E 50/16* (2013.01)

(58) Field of Classification Search
None
See application file for complete search history.

(56) References Cited

U.S. PATENT DOCUMENTS

| | | |
|---|---|---|
| 7,985,890 B2 | 7/2011 | Basu |
| 2004/0123343 A1* | 6/2004 | La Rosa .............. C07K 14/415 800/278 |
| 2004/0181830 A1 | 9/2004 | Kovalic et al. |
| 2007/0061916 A1 | 3/2007 | Kovalic et al. |
| 2010/0017916 A1 | 1/2010 | Pappan et al. |
| 2011/0093965 A1* | 4/2011 | O'Donoghue .......... C12N 9/16 800/14 |
| 2011/0154530 A1 | 6/2011 | Bläsing et al. |
| 2012/0005770 A1 | 1/2012 | Hertzberg et al. |

FOREIGN PATENT DOCUMENTS

| | | |
|---|---|---|
| WO | 2009146464 A2 | 12/2009 |
| WO | 2010020654 A2 | 2/2010 |
| WO | 2010062240 A1 | 6/2010 |
| WO | 2013167902 A1 | 11/2013 |

OTHER PUBLICATIONS

Lin et al (2001 The institute for genomic research, locus AC019018.*
McClellan et al., Genetic screening for genes in *Arabidopsis thaliana* that improve sugar release from plant lignocellulose, Internet Citation, Jan. 1, 2010, p. 1, retrieved from the Internet: URL:http://gcep.stanford.edu/pdfs/v15Z1pJh8XCevgvx1PJO-g/Christopher_McClellan_Poster2010.pdf.
Vanholme et al., Potential of Arabidopsis systems biology to advance the biofuel field, Trends in Biotechnology, Nov. 1, 2010, pp. 543-547, vol. 28, No. 11.
Usadel et al., Co-expression tools for plant biology: opportunities for hypothesis generation and caveats, Plant, Cell & Environment, Dec. 1, 2009, pp. 1633-1651, vol. 32, No. 12.
Jung et al., Modifying crops to increase cell wall digestibility, Plant Science, Apr. 1, 2012, pp. 65-77, vol. 185-186.
Kavousi et al., Consequences of antisense down-regulation of a lignification-specific peroxidase on leaf and vascular tissue in tobacco lines demonstrating enhanced enzymic saccharification, Phytochemistry, Apr. 1, 2010, pp. 531-542, vol. 71, No. 5-6.
Abramson et al., Plant cell wall reconstruction toward improved lignocellulosic production and processability, Plant Science, Feb. 1, 2010, pp. 61-72, vol. 178, No. 2, Elsevier Ireland Ltd, IE.
Buanafina et al., Abstract, Targeting expression of a fungal ferulic acid esterase to the apoplast, endoplasmic reticulum or golgi can disrupt feruloylation of the growing cell wall and increase the biodegradability of tall fescue (*Festucs arundinacea*), Plant Biotechnology Journal, Apr. 1, 2010, vol. 8, No. 3.
Buanafina et al., Targeting expression of a fungal ferulic acid esterase to the apoplast, endoplasmic reticulum or golgi can disrupt feruloylation of the growing cell wall and increase the biodegradability of tall fescue (*Festucs arundinacea*), Plant Biotechnology Journal, Apr. 1, 2010, vol. 8, No. 3.

* cited by examiner

*Primary Examiner* — Brent T Page
(74) *Attorney, Agent, or Firm* — TraskBritt, P.C.

(57) ABSTRACT

The disclosure is based on the discovery of genes which influence lignin biosynthesis. In particular, the inventors have observed that if the expression, function and/or activity of these gene(s) (or any protein products thereof) is/are modulated, the lignin content of plants can be altered. As such, this disclosure provides plants, which exhibit modulated expression of one or more lipase/esterase/thioesterase family gene(s) and which may find application in methods for producing biofuels.

7 Claims, 15 Drawing Sheets

Figure 1A:
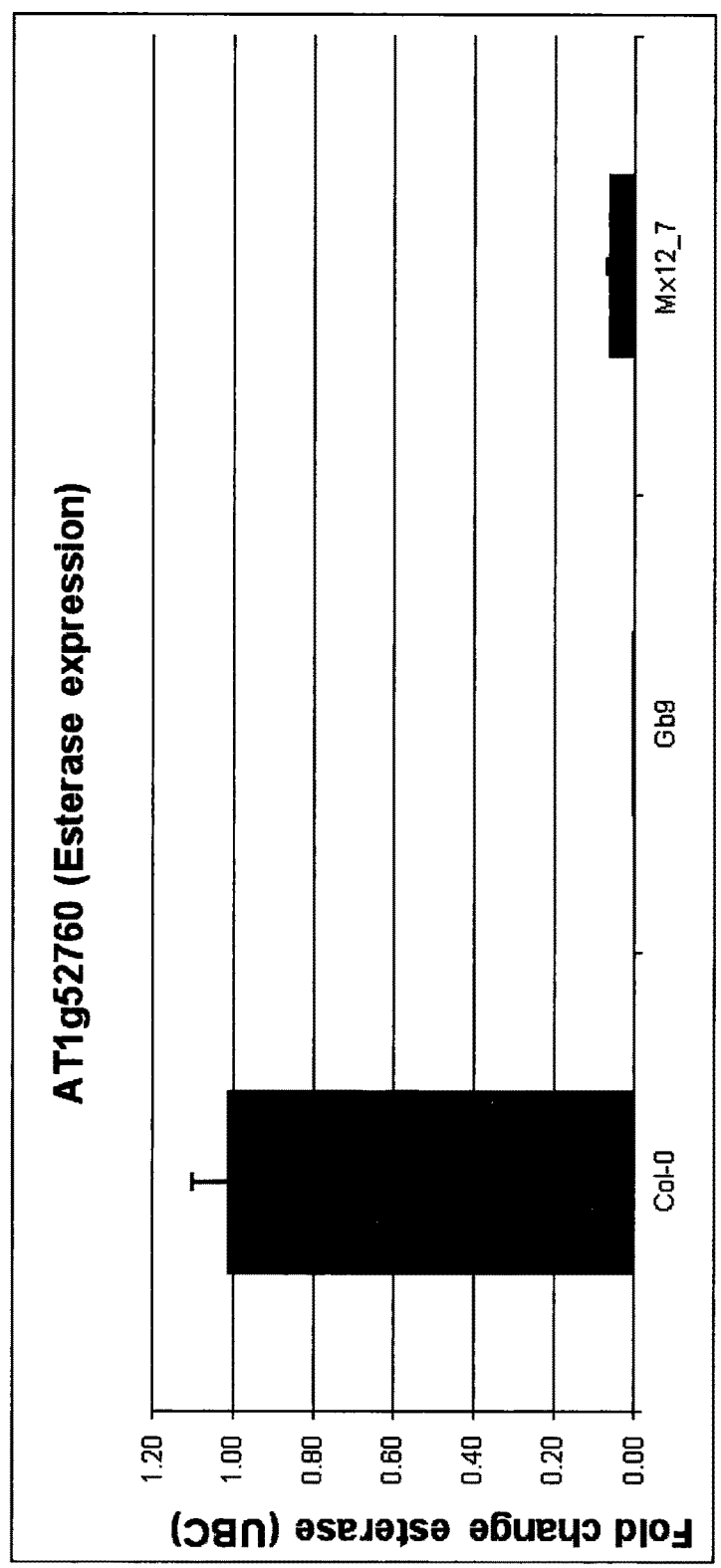

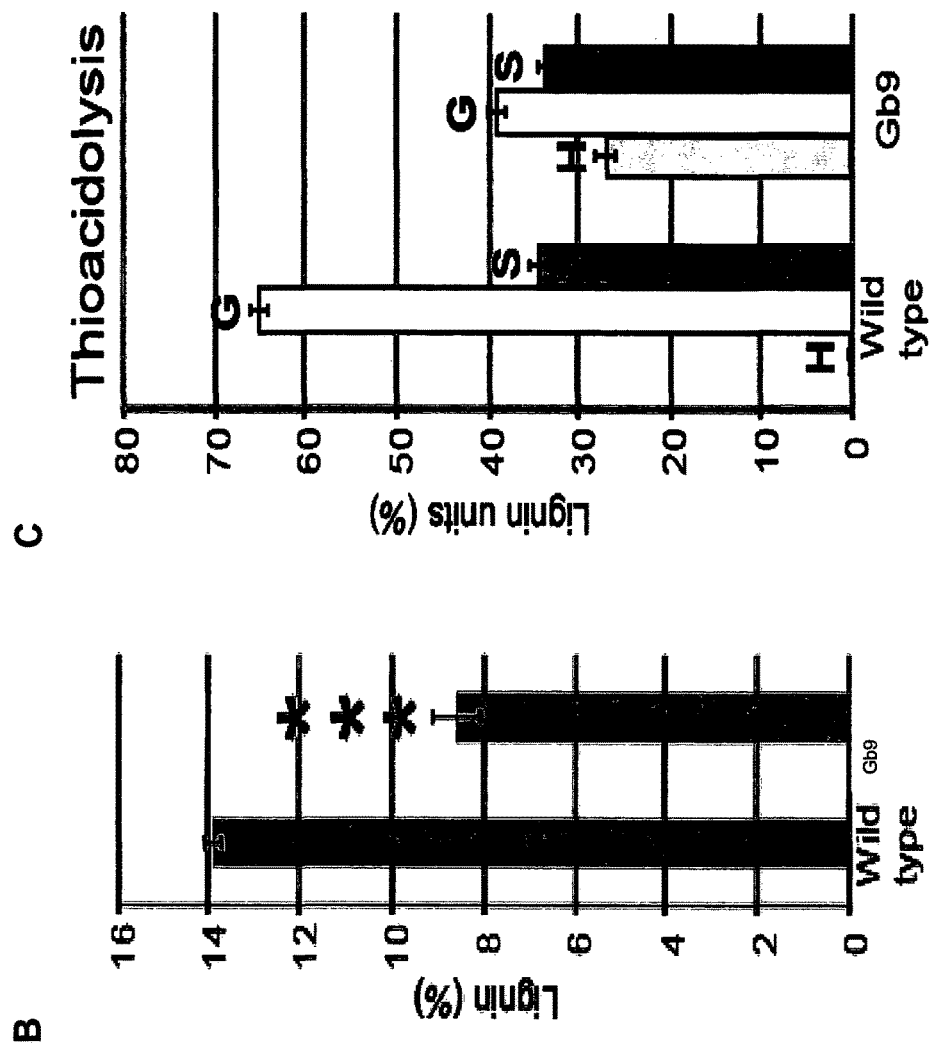
Figure 3B and C

Figure 9

METHOD FOR MODIFYING LIGNIN BIOSYNTHESIS IN PLANTS

CROSS-REFERENCE TO RELATED APPLICATIONS

This application is a national phase entry under 35 U.S.C. §371 of International Patent Application PCT/GB2013/051206, filed May 9, 2013, designating the United States of America and published in English as International Patent Publication WO 2013/167902 A1 on Nov. 14, 2013, which claims the benefit under Article 8 of the Patent Cooperation Treaty and under 35 U.S.C. §119(e) to Great Britain Application Serial No. 1208105.5 filed May 9, 2012.

TECHNICAL FIELD

The disclosure provides modified plants having altered lignin and the use of such plants in processes which require carbohydrate extraction from plants, including, for example, methods for the production of biofuels.

BACKGROUND

Lignin is a phenolic polymer made from monolignol units that strengthens and waterproofs plant cell walls and influences the downstream processing of plant biomass for agricultural and industrial processes. For example, the presence of lignin in biomass makes it harder for enzymes to gain access to cell wall polysaccharides (cellulose and hemicellulose) in order to release the component sugars for useful purposes such as biofuel, bioplastic or chemical production. Much research effort has focused on manipulating the lignin pathway to make it easier to process biomass for these kinds of applications [1]. Although the monolignol biosynthesis pathway is well-characterized, there are still novel genes involved in lignification that remain to be discovered. For example, two laccases have recently been identified as being involved in lignin synthesis [2]. Other genes that are directly or indirectly involved in lignification that could be targets for useful manipulation remain to be identified.

BRIEF SUMMARY

The disclosure is based on the discovery of genes that influence lignin biosynthesis. In particular, the inventors have observed that if the expression, function and/or activity of these gene(s) (or any protein products thereof) is/are modulated, the lignin content of plants can be altered.

As such, a first aspect of this disclosure provides a plant exhibiting modulated expression of one or more lipase/esterase/thioesterase family gene(s), wherein the plant comprises a modified lignin.

For convenience, the plants provided by this disclosure shall be referred to hereinafter as "modified" plants.

The phrase "modulated expression of a lipase/esterase/thioesterase family gene(s)" should be understood as encompassing any increase or decrease in the expression of one or more gene(s) belonging to the lipase/esterase/thioesterase family. One of skill will appreciate that levels of gene expression in modified plants of this disclosure may be assessed relative to the expression of a corresponding gene in a control plant of the same species. A control plant may, for example, be a wild-type plant exhibiting a wild-type level of expression of a/the corresponding lipase/esterase/thioesterase family gene(s). It should be understood that modulated gene expression may be detected by quantitative and/or qualitative comparison of gene expression levels between modified plants of this disclosure and control plants.

The methods by which levels of gene expression can be assessed are well known to one of skill and include, for example, PCR based techniques including real-time PCR and the like. Northern Blotting techniques may also be used. Further information on such techniques may be found in Molecular Cloning: A Laboratory Manual (Third Edition) By Sambrook, MacCallum & Russell, Pub. CSHL; ISBN 978-087969577-4, incorporated herein by reference.

As stated, the modified plants provided by this disclosure comprise an altered or modified lignin, that is to say, when compared to a control plant (or population of control plants) having a known, standard or wild-type lignin, the modified plants of this disclosure comprise either more or less lignin and/or lignin having an altered or variant structure/composition. As such, references to "modified plants" or "modified lignin" or "altered lignin" should be taken to encompass plants which, when compared to un-modified plants of the same type (i.e., plants which exhibit wild-type or normal levels of lipase/esterase/thioesterase family gene expression), comprise more or less lignin (i.e., plants which exhibit a modified or altered lignin content) or lignin having an altered or modified composition/structure.

Regarding lignin structure and/or composition, it should be understood that lignin is largely comprised of hydroxycinnamyl alcohols—more commonly referred to as the monolignols coniferyl alcohol (the G-lignin unit), sinapyl alcohol (the S-lignin unit) and p-coumaryl alcohol (the H-lignin unit). The precise lignin structure/composition varies from plant to plant; for example, grasses may comprise lignin, which comprises an elevated amount of H-unit lignin whereas lignins from gymnosperms may be composed of G-units only. As such, references to altered or modified lignin composition and/or structure may encompass lignin, which in comparison to the lignin of an un-modified form of a particular plant, exhibits an altered H, G and/or S unit composition. By way of example, lignins from the modified plants described herein may comprise different proportions of H, G and S-units as compared to the lignins of un-modified forms of the same plants. A modified plant of this disclosure may comprise an altered S-unit composition. A modified plant of this disclosure may comprise an altered H, G and/or S unit composition and the amount or proportion of H, G and/or S units might increase or decrease. For example, the amount or proportion of H units might increase and the amount and/or proportion of S and G units might decrease.

In addition to the various structural and compositional modifications described above, it should be understood that the term "modified lignin" may further include modified lignin which, relative to a comparable wild-type plant, comprises one or more unusual monomers and/or increased amounts thereof [3-5].

This disclosure provides plants exhibiting reduced expression of one or more lipase/esterase/thioesterase family gene(s), wherein the plants comprise a reduced or modified lignin; the reduced expression of the lipase/esterase/thioesterase family gene(s) and associated modified lignin, being assessed relative to the lipase/esterase/thioesterase family gene expression and lignin of a control plant having a known or quantified level of lipase/esterase/thioesterase family gene expression and/or lignin.

Lignin is predominantly deposited in the cell wall making them rigid and impermeable and protecting the cell wall polysaccharides from microbial degradation.

In wild-type plants, the presence of lignin in plant cell walls and other structures protects plant carbohydrates rendering them inaccessible to hydrolysing enzymes, etc., this makes methods which require the release of sugars from lignin-containing plant matter (for example, methods of biofuel production), inefficient and costly.

The cell walls and vascular structures of the modified plants described herein may comprise less lignin and/or a modified lignin and one advantage associated with such plants is that material or biomass derived therefrom may be more easily deconstructed to access carbohydrate polymers and enable the release of sugars.

As such, modified plants, according to the first aspect of this disclosure, may find application in methods for accessing and/or processing carbohydrate polymers from plant matter and, for example, biofuel production.

In view of the above, biomass derived from plants modified in accordance with this disclosure may be used as feedstock for processes which require or exploit plant cell wall carbohydrates. By way of example, biomass derived from the modified plants of this disclosure may be used in biofuel production methods.

In one embodiment, and through the teachings of this disclosure, biomass for use in methods involving plant carbohydrate deconstruction (for example, biofuel production) may comprise, for example, parts of crops, waste crop material and trees, all of which may be regarded as typically high in lignin.

The term "plant," as used herein, may comprise a crop or grass species, hybrids and varieties including, for example, those belonging to the *Saccharum, Zea, Triticum, Secale, Hordeum, Glycine, Oryza, Sorghum, Lolium, Vitis* and *Medicago* genera. In addition, the term "plant" may encompass species, hybrids and varieties of the *Miscanthus, Panicum* (switchgrass), *Phalaris* (reed canary grass), *Cannabis* (hemp) genera—plants of this type may be grown as crops for use in bioenergy production (i.e., as dedicated bioenergy crops). In other embodiments, the term "plant" encompasses species, hybrids and varieties of trees such as *Salix, Populus*, and *Eucalyptus* genera.

In view of the above, it should be understood that the "plant biomass" for use in methods requiring or exploiting plant cell wall carbohydrates, for example, biofuel production, may comprise material or matter derived from modified forms (i.e., forms exhibiting modulated expression of one or more lipase/esterase/thioesterase family gene(s)) of any of the plants described herein.

One of skill will appreciate that the term "biomass" may comprise any part of a plant, including, for example, the stem, flower (including seed heads, etc.), root and leaves. Where a modified plant provided by this disclosure exhibits modified lignin content throughout its cells and tissues, any part of that plant may yield biomass, which is useful as feedstock for methods requiring plant carbohydrate extraction or methods of producing biofuel—of particular use are the stems, leaves and roots.

In other embodiments, the modulated expression of one or more lipase/esterase/thioesterase family gene(s) and/or the modified lignin may be confined to one or more specific parts or tissues of a plant. For example, the modulated expression of a lipase/esterase/thioesterase family gene and/or modified lignin content may be apparent in one or more of the cells or tissues—including, for example, the meristem, stem, root, pistil, anther, flower, leaf, seed, embryo, stalk and/or petiole. In such cases, the parts comprising modified lignin will be most useful as feedstock for methods requiring or exploiting plant carbohydrates or, for example, biofuel production processes.

In one embodiment, a lipase/esterase/thioesterase family gene may encode a lysophospholipase and/or esterase enzyme. Thus, this disclosure may provide a plant exhibiting modulated expression of one or more lysophospholipase and/or esterase gene(s) and/or one or more lysophospholipase and/or esterase enzymes, wherein the plant comprises a modified or altered lignin.

One of skill will appreciate that modulation of lysophospholipase and/or esterase gene expression may result in a corresponding increase or decrease in lysophospholipase and/or esterase enzyme expression. A modulated level of lysophospholipase and/or esterase enzyme expression may be determined relative to a level of lysophospholipase and/or esterase enzyme expression in a control plant having a known or quantified level of lysophospholipase and/or esterase enzyme expression. As stated above, a control plant may take the form of a wild-type plant of the same species, the wild-type plant exhibiting a wild-type level of lipase/esterase gene expression.

In some embodiments, the disclosure provides a plant exhibiting reduced expression of one or more lysophospholipase and/or esterase gene(s), wherein the plant comprises a modified lignin.

In a further embodiment, the disclosure provides a plant exhibiting reduced expression of one or more lysophospholipase and/or esterase protein/enzymes, wherein the plant comprises a modified lignin. One of skill will appreciate that any reduction in the function, activity and/or expression of one or more lipase/esterase/thioesterase family gene(s), may result in an associated (or corresponding) reduction in the function, activity and/or expression of the encoded lysophospholipase and/or esterase. This in turn may result in a plant comprising a modified or altered lignin.

The plant may be *Arabidopsis thaliana* and the lysophospholipase and/or esterase gene is the lysophospholipase 2 gene designated LysoPL2 and encoding lysophospholipase 2. An exemplary *A. thaliana* LysoPL2 gene has been deposited under the accession number AT1G52760 and has the sequence designated SEQ ID NO:1 below:

```
                                                        SEQ ID NO: 1
  1    CTTTATCACC ACCAAAAACC AAAATTCACT GCCAAAAAAA ACACATCAAA

51    ACGATGCCGT CGGAAGCGGA GAGCTCAGCG AATTCAGCTC CGGCAACTCC

101    GCCACCACCA CCGAATTTCT GGGGAACCAT GCCGGAGGAA GAGTACTACA

151    CTTCACAAGG AGTACGTAAC AGCAAATCAT ACTTCGAAAC ACCAAACGGC

201    AAGCTCTTCA CTCAGAGCTT CTTACCATTA GATGGTGAAA TCAAAGGCAC
```

```
-continued
 251   TGTGTACATG TCTCATGGAT ACGGATCCGA TACAAGCTGG ATGTTTCAGA

301   AGATCTGTAT GAGTTTCTCT AGTTGGGGTT ACGCTGTTTT CGCCGCCGAT

351   CTTCTCGGTC ACGGCCGTTC CGATGGTATC CGCTGCTACA TGGGTTCGTT

401   TACTTCGTTC CTCTGTTTTG ATAAGATAAA TTTTCCATCT TTGTGTAATT

451   GATAAGATAA TTTACGATCT TTAGGTGATT AAAGATTGGA TTTTTATGGT

501   TATTAGGTGA TATGGAGAAA GTTGCAGCAA CATCATTGGC TTTCTTCAAG

551   CATGTTCGTT GTAGTGATCC ATATAAGGAT CTTCCGGCTT TTCTGTTTGG

601   TGAATCGATG GGAGGTCTTG TGACGCTTTT GATGTATTTT CAATCGGAAC

651   CTGAGACTTG GACCGGTTTG ATGTTTTCGG CTCCTCTCTT TGTTATCCCT

701   GAGGATATGA AACCAAGCAA GGCTCATCTT TTTGCTTATG GTCTCCTCTT

751   TGGTTTGGCT GATACGTGGG CTGCAATGCC GGATAATAAG ATGGTTGGGA

801   AGGCTATCAA GGACCCTGAA AAGCTTAAGA TCATCGCTTC TAACCCGCAA

851   AGGTACTATT AAACTTCTTG GAAGCAAACA TAGTATAAAG CTTGAGACTT

901   TACTTTGGAA GCTATAAAAG TTTGGATTTT GCATTGTAGA TATACAGGGA

951   AGCCTAGAGT GGGAACAATG AGAGAGTTAC TGAGGAAGAC TCAATACGTT

1001   CAGGAGAATT TCGGGAAAGT TACTATTCCG GTGTTTACGG CGCACGGGAC

1051   AGCGGATGGA GTAACATGTC CTACATCTTC GAAGCTACTA TACGAAAAAG

1101   CGTCAAGCGC TGATAAAACG TTGAAGATCT ATGAAGGGAT GTATCACTCG

1151   CTGATTCAAG GAGAGCCTGA CGAGAACGCT GAGATAGTCT TGAAGGATAT

1201   GAGAGAGTGG ATCGATGAGA AGGTTAAGAA GTATGGATCT AAAACCGCTT

1251   GAACAAAGCT ACATTTGTGT TACAAGAACT TGAAGAGAAA TGTATATTGA

1301   TGTTATGATC CGTATCGTCG ATTTGACTTG TTTTGTTGTC TGTTGTAATC

1351   CAAGAACATG AATTTTCTGA TGTAAGAACT TATAATATCA TGGATTACAG

1401   AAATCCTTTT ATCATTTCT
```

The protein encoded by this sequence is provided below as SEQ ID NO:2.

```
                                            SEQ ID NO: 2
   1   MPSEAESSAN SAPATPPPPP NFWGTMPEEE YYTSQGVRNS KSYFETPNGK

51   LFTQSFLPLD GEIKGTVYMS HGYGSDTSWM FQKICMSFSS WGYAVFAADL

101   LGHGRSDGIR CYMGDMEKVA ATSLAFFKHV RCSDPYKDLP AFLFGESMGG

151   LVTLLMYFQS EPETWTGLMF SAPLFVIPED MKPSKAHLFA YGLLFGLADT

201   WAAMPDNKMV GKAIKDPEKL KIIASNPQRY TGKPRVGTMR ELLRKTQYVQ

251   ENFGKVTIPV FTAHGTADGV TCPTSSKLLY EKASSADKTL KIYEGMYHSL

301   IQGEPDENAE IVLKDMREWI DEKVKKYGSK TA
```

One of skill will appreciate that functionally equivalent sequences and/or sequences identical or similar to, or homologous or orthologous with, the lysophospholipase and/or esterase sequences described herein, in particular the sequences given as SEQ ID NOS: 1 or 2 above (or a fragment thereof), may be present in other plant species. Examples of such sequences are given below for *Populus trichocarpa, Vitis vinifera, Glycine max, Medicago truncatula, Oryza sativa, grandis* and *Panicum virgatum*. These exemplary protein sequences have been deposited under the accession numbers XP_002303266.1, CAN62561.1, XP_002298118.1, XP_003542674.1, XP_003610038.1, EAY84954.1, Eucgr.F02557, Pavirv0007801m.1 and have the sequence designated SEQ ID NOS:3-18 below:

*Populus trichocarpa* predicted protein, mRNA. ACCESSION XM_002303230

SEQ ID NO: 3

```
   1 tcctccctcc cgcaaccagt tttaaaaaaa gttgaaacac cattatccaa ctccgaaacg
  61 ccacccacct actccctgta aaaaacccct accgttttct ctgtttaaaa gtcaaccatc
 121 caagccttac gataaccgta acgagacgtg accatgccat ccgaagcgca gcagcccgaa
 181 gcgccaccca acttctgggg cgacatgccg gaggaggagt actatgcatc gcaaggagtg
 241 accaataccc agtcacactt tgaaacgccg aatgggaagg tcttcacgca gggttttctc
 301 ccgttggata aaaaggtcaa agccacggtg tatatgaccc acggctacgg atctgatact
 361 ggctggctgt ttcagaagat ttgcatcaac tttgctacct ggggttatgc tgttttgct
 421 gctgatcttc ttgggcatgg cagatcagac ggtttacgct gctacatggg cgacatggag
 481 aaaattgctg cagcgtccgt atcgttcttc aagcatgtgc gctacagcga gccatacaag
 541 aacttgcccg ccttcttatt tggcgagtca atgggcggac tagcaacgat gctgatgtat
 601 ttccaatcag aacctgacac gtggacgggc gtgattttct cggcccccact tttcgtcata
 661 ccggaaccaa tgaaacctag taaggcacac ctattcatgt atggcctgct ctttggattt
 721 gctgacacgt gggcggccat gccagacaac aaaatggtag gtaaagcgat aaaggaccca
 781 gagaaactca agatcatagc atccaaccce agaagataca caggcaagcc tagggtgggt
 841 accatgagag aaattgccag agtctgccaa tacatacagg acaatttctc caaggttacg
 901 gtgccgtttt tgactgtcca cgggaccgcc gatggggtga catgcccaac atcatcacag
 961 ttgttgtatg agaaagcctc gagtgaggat aagagcttga agatgtacga gggcatgtac
1021 cattctttga tacaaggcga gcctgacgaa aatgcaagtc ttgtcttgaa ggatatgaga
1081 gagtggatcg atgagagggt tgagaggtat gggtctacaa agagtgatga ttgaaatcat
1141 atatgaagaa aaaatggtgg ttttttttct ggaaaagtga agcttggtcc atagtctctt
1201 gatgggatta gggcaaaacg aatgccaatg taattgaata attttgaact aacgaagtca
1261 gctattgctt ctctcgattt aatttataaa aaaaatgttt gaacttttta attttc
```

The protein encoded by this sequence is provided below as SEQ ID NO:4.

Predicted protein [*Populus trichocarpa*] ACCESSION XP_002303266

SEQ ID NO: 4

```
  1 mpseaqqpea ppnfwgdmpe eeyyasqgvt ntqshfetpn gkvftqgflp ldkkvkatvy
 61 mthgygsdtg wlfqkicinf atwgyavfaa dllghgrsdg lrcymgdmek iaaasysffk
121 hvrysepykn lpaflfgesm gglatmlmyf qsepdtwtgv ifsaplfvip epmkpskahl
181 fmygllfgfa dtwaampdnk mvgkaikdpe klkiiasnpr rytgkprvgt mreiarvcqy
241 iqdnfskvtv pfltvhgtad gvtcptssql lyekassedk slkmyegmyh sliqgepden
301 aslvlkdmre widververyg stksdd
```

*Populus trichocarpa* predicted protein, mRNA. ACCESSION XM_002298082

SEQ ID NO: 5

```
  1 atgtcatccg aaacgcagca acccgaaacg cctcccaact tctggggcga catgccggag
 61 gaggagtact atgcgtcaca aggagtgacc actacccaat catacttcga gacgccaaat
121 gggaagctct tcacgcaagg ttttctcccg ttggataaaa aagtcaaagc cacggtatat
181 atgacccacg gctatggatc tgatactggc tggttgttcc agaagatttg catcagcttt
241 gctaactggg gttatgctgt ttttgccgct gatcttcttg gacatggcag atcagacggt
301 atacgttgct acatgggtga catggacaag attgctgcca cttccctgtc attcttcaag
361 cacgagcgct tcagcgaacc atacaagggc ttaccagcct tcttatttgg tgaatcaatg
```

-continued

```
421 ggtggactca caacaatgct aatgtacttc caatcagaac ctaacatgtg gacgggcttg 481 attttctcgg cgccactttt tgtcatacca gaagcgatga aaccaagcaa ggtacaccta 541 ttcatgtatg gcctgctctt tggattggct gatacgtggg cagccatgcc agacaacaaa 601 atggtaggca aagcgatcaa ggacccagag aagctcaaga tcatagcatc caacccctagg 661 agatacacag gcaagcctag ggtgggaacc atgagggaaa ttgctaggat gtgccaatac 721 atacaggaca atttctccaa ggttacagcg ccgttcttga cagtccacgg cacggctgat 781 ggggtgacat gccctacatc atcacagttg ttgtttgaga aagcctctag tgaggacaag 841 agcttgaaga tgtacgaggg catgtaccat tctttgatac aaggtgagcc cgatgagaat 901 gctaatcttg ttttgaagga tatgagaggg tggattgacg agagggttga gaggtatggg 961 tccaaaaaaa gcgatgactg a
```

The protein encoded by this sequence is provided below as SEQ ID NO: 6.

```
Predicted protein [Populus trichocarpa] ACCESSION XP_002298118
                                                        SEQ ID NO: 6
  1 mssetqqpet ppnfwgdmpe eeyyasqgvt ttqsyfetpn gklftqgflp ldkkvkatvy 61 mthgygsdtg wlfqkicisf anwgyavfaa dllghgrsdg ircymgdmdk iaatslsffk 121 herfsepykg lpaflfgesm gglttmlmyf qsepnmwtgl ifsaplfvip eamkpskvhl 181 fmygllfgla dtwaampdnk mvgkaikdpe klkiiasnpr rytgkprvgt mreiarmcqy 241 iqdnfskvta pfltvhgtad gvtcptssql lfekassedk slkmyegmyh sliqgepden 301 anlvlkdmrg widerveryg skksdd EMBL-CDS: CAN62561.1: Vitis vinifera hypothetical protein
                                                        SEQ ID NO: 7
  1 atgtcgtcgg aatccgaaat tcggccaac ttctggggcg atatgccgga ggaggagtac 61 tatgcctccc aaggggtgcg caacaccaaa tcatayttcg acaccccaa cggcaagctc 121 ttcacccaga gtttcctacc cttggatctc cctgtcaagg cttccgtcta catgacccac 181 ggctacggct ccgacaccgg ctggctcttc cagaagattt gcattaacta cgccacctgg 241 ggctacgcag tcttcgccgc cgacatcctc ggccacggcc gctccgacgg yatccgctgc 301 tacctcggcg acatggagaa ggtcgccgcc acctcccttt cyttcttcaa gagcgtycgc 361 accagcgaat cctaccgyga cctccctgct ttcctcttcg gcgagtccat gggtggggct 421 accaccatgc tcgtgtactt ccaatcggag ccggagctgt ggacaggcct gatcttctca 481 gccccacttt tcgtgatgcc ggagaacatg aagccgtcga aggtgaggct attcctgtac 541 ggacttctgt ttgggatggc tgacacgtgg gcgacgatgc cggacaacaa gatggtgggg 601 aaggcgatca aggatccgga gaagctgaag gtcatagcgt cgaatccacg gcggtacacg 661 ggtccgccga gggtggggac gatgagggag ctggctaggg tgtgccagta catacaggat 721 aatttctcga argtgackgc gccgttcttg acggtgcacg gacggcrga tggggtgacg 781 tgtccgacgt cgtcgaagct gctgtacgag aaggcttcga gtgaggacaa agcattgaag 841 ttgtatgagg ggatgtacca ttctttgata cagggagagc ctgatgagaa tkccaatctg 901 gtgttgaagg atatgaggga atggattgat gagagggttg agagatacgg accctccaaa 961 tcctag
```

The protein encoded by this sequence is provided below as SEQ ID NO:8.

```
Hypothetical protein VITISV_001366 [Vitis vinifera]. ACCESSION CAN62561
                                                         SEQ ID NO: 8
    1 msseseisan fwgdmpeeey yasqgvrntk syfdtpngkl ftqsflpldl pvkasvymth 61 gygsdtgwlf qkicinyatw gyavfaadil ghgrsdgirc ylgdmekvaa tslsffksvr 121 tsesyrdlpa flfgesmgga ttmlvyfqse pelwtglifs aplfvmpenm kpskvrlfly 181 gllfgmadtw atmpdnkmvg kaikdpeklk viasnprryt gpprvgtmre larvcqyiqd 241 nfskvtapfl tvhgtadgvt cptsskllye kassedkalk lyegmyhsli qgepdenxnl 301 vlkdmrewid erverygpsk s Monoglyceride lipase [Medicago truncatula] (MTR_4g127220) mRNA. ACCESSION
XM_003609990
                                                         SEQ ID NO: 9
    1 aatctctaat tatccatcct cacccgtttc catcgctgaa acaacaacgc caatggcaac 61 gcagcaggaa tcagagattc ccccaaattt ctggggtcac acccccgaag aagaatacta 121 cacctcccaa ggagttcgca ataccaaatc acacttcgaa acacccaacg gcaaaatctt 181 cacacagtcc tttctcccac tcaacgctga aatcaaagct accgtttaca tgactcacgg 241 ttacggctcc gacaccggct ggctcttcca aaaaatctgc atcacctacg ccacctgggg 301 ttacgccgtc ttcaccgctg atctcttagg tcacggccgt tccgatggcc tccgttgcta 361 cctcggggac atggacaaaa tcgccgccac ctcactttca ttttcctcc acgtccgccg 421 ttctcctccc tacaaccacc tcccagcgtt tctcttcggt gagtcaatgg gtggtttagc 481 tacattgctg atgtatttcc aatcagaacc cgacacgtgg acgggtttaa tattctcagc 541 gccgcttttc gtaatccccg aggatatgaa accgagtaag attcatttgt ttgtgtacgg 601 tcttttgttt ggtttggctg acacgtgggc agcgatgcct gataacaaaa tggtcggaaa 661 agcaattagg gatccaaata agttgaagat tattgcttct aatccaagga ggtatacggg 721 cccacctaga gtagggacca tgagggaact tcttagagtc actcaatatg tgcaagataa 781 tttctgcaat gtaacggtgc cgtttcttac ggcacatggt actgctgatg tgtcacgtg 841 cccttcttct tctaagctgt tgtatgagaa agctgaatct aaggataaga ctttgaagct 901 ttatgagggg atgtatcatt ctttgattca aggggagcct gatgagtctg ctaatcttgt 961 gttaagggat atgagggagt ggattgatga gagggttcgt aggtatggac ctaataatga 1021 taattctcaa tgaaaaacaa gggtggctgt tgtgtttttt tttcatacaa tttttagttt 1081 ggaattacct ggtctcgata atcaagattt gattgaggac tattgttatg actatattga 1141 aattttatg actatatgaa cgaactgtga tgttgttata tggtgtgctt cgtttagatc 1201 cttctataca taacaatatg atcttacggt tc
```

The protein encoded by this sequence is provided below as SEQ ID NO:10.

```
ACCESSION XP_003610038.1
                                                         SEQ ID NO: 10
    1 matqqeseip pnfwghtpee eyytsqgvrn tkshfetpng kiftqsflpl naeikatvym 61 thgygsdtgw lfqkicitya twgyavftad llghgrsdgl rcylgdmdki aatslsfflh 121 vrrsppynhl paflfgesmg glatllmyfq sepdtwtgli fsaplfvipe dmkpskihlf 181 vygllfglad twaampdnkm vgkairdpnk lkiiasnprr ytgpprvgtm rellrvtqyv 241 qdnfcnvtvp fltahgtadg vtcpssskll yekaeskdkt lklyegmyhs liqgepdesa 301 nlvlrdmrew idervrrygp nndnsq
```

-continued

```
PREDICTED: Glycine max monoglyceride lipase-like (LOC100785661),
mRNA. ACCESSION XM_003542626
                                                        SEQ ID NO: 11
   1 acccaatcgc aatggcaccg gaatcagagg ctcccctaa cttctggggc cacaccccgg 61 aagaagaata ctacacctcc caaggcgttc gcaacaccaa gtcccacttc gaaaccccca 121 acggcaaaat cttcacccag tccttcctcc ctctcaacct ccaacccac caagtcaaag 181 ccaccgtctt tatgacccac ggctacggct ccgacaccgg ctggctcttc cagaaaatct 241 gcatcaactt cgccacctgg ggctacgccg tcttcgccgc cgacctcctc ggccacggcc 301 gctccgacgg tctccagtgc tacctcggcg acatggacaa aatcgccgcc acctccctct 361 ccttcttcct ccacgtccgc aatagccacc cctacaaaaa cctcccggca ttcctcttcg 421 gcgagtccat gggaggactc gccacgctcc tcatgtactt caaatcggaa ccggacacgt 481 ggacgggcct gatgttctcc gcgccactct tcgtgattcc cgaggacatg aaacccagca 541 gggtacattt gttcatgtac ggtctcttgt tcggtctcgc cgacacgtgg gcggccatgc 601 cggataacaa aatggtcgga aaggccatca gggatcccga gaagttgaag gtcatagcgt 661 cgaacccgag gcgctacacg ggcccaccca gggtggggac catgcgggag ctgcttaggg 721 tgacacagta tgtacaggat aatttctcca aggtaacgac gccgttttc actgctcacg 781 gaacttctga cggcgttacc tgcccttcct cgtccaagct gctgtatgag aagggttcca 841 gtgaggataa gacgttgaag ctctacgatg gaatgtatca ctctttgatt cagggagagc 901 ccgatgagtc tgcgaatctc gtgttggggg acatgagaga gtggattgat gagagggttc 961 gacggtatgg acctaacaaa aattcccagt gaaacaaacc attactaaat tcctattttg 1021 gttccacatt gcatattttg tgtctatcaa aactttatta aagttgttat gtgaagacgg 1081 aagagtatcc ttcttctatc atatttggat ttcaatcaaa aatgacattt aatcaatcca 1141 gttatcggtt tcgatgcatg attaacttta gtcctaatct ctcaggatat agtagtaata 1201 aattcctcat agtccaggtt tcaaagttta tattagtcga aaaattatgt gaaacctaag 1261 gaagtttaca aaaatcagat agagagagat atttc
                                        40
```

The protein encoded by this sequence is provided below as SEQ ID NO:12.

```
PREDICTED: monoglyceride lipase-like [Glycine max] ACCESSION XP_003542674
                                                        SEQ ID NO: 12
   1 mapeseappn fwghtpeeey ytsqgvrntk shfetpngki ftqsflplnl qphqvkatvf 61 mthgygsdtg wlfqkicinf atwgyavfaa dllghgrsdg lqcylgdmdk iaatslsffl 121 hvrnshpykn lpaflfgesm gglatllmyf ksepdtwtgl mfsaplfvip edmkpsrvhl 181 fmygllfgla dtwaampdnk mvgkairdpe klkviasnpr rytgpprvgt mrellrvtqy 241 vqdnfskvtt pfftahgtsd gvtcpssskl lyekgssedk tlklydgmyh sliqgepdes 301 anlvlgdmre widervrryg pnknsq.
EMBL-CDS: EAY84954.1: Oryza sativa Indica Group hypothetical protein
                                                        SEQ ID NO: 13
   1 atggcgccgccaccgccgccaccgacggcgacgaagtacttctggggcgactccccggag 61 cccgacgagtactacgcctcgctgggtctccgccacgccgaggcctacttccagtccccc 121 tgcggccgcctcttcacgcactcgttccaccgctctccgccgccagcgacggcgacgtc 181 aagggcgtcgtcttcatgagccacggctacggctccgactcctcgtggatgttccagaac 241 atcgccatcagctacgcgcggtggggtacgccgtcttctgcgccgacctgctcggacac 301 ggccgctccgacggcgtccgcggctacctcggcgacacggaggccgtcgcgagggcggcg
```

-continued

```
361 ctctccttcttcctctccgtgcggcggagcggcgcctacgcctccctcccggcgttcctc 421 ttcggcgagtccatgggcggcgccaccaccctgctcgcctacctccgctccccgcccgac 481 gccgggtgggcggggatcatcctgtcggcgccgctgctcgtcttccccgacgacatgtac 541 ccgtcccgcgtgcggctcttcctgtacggcctcctcttcggtctagccgacacatgggcg 601 gtgatgccggacaagaggatggtggggagatcgatccgcgacccggcgaagctgagggtg 661 atcgcgtccaacccgcggctgtaccgcggctcgccgcgggtggggacgatgcgggagctc 721 gcacgcgtgacggcgctgctgcgggagagcttcggggaggtggcggcgccgttcctggtg 781 gtgcacggcaccgacgacggggtgacctcgccggaggggtccaggatgctgtacgagcgc 841 gcggcgagcgaggacaagagcctcatcctctacgacgggatgtaccactcgctcatccag 901 ggggagtccgacgagaaccgcgaccgcgtgctcgccgacatgcgcgcctggatcgacgag 961 cgcgtccgccgctacggcgccggcgccggcgccgcggcgg
```

The protein encoded by this sequence is provided below as SEQ ID NO:14.

```
Putative uncharacterized protein A2X294 (A2X294_ORYSI)
                                                    SEQ ID NO: 14
  1 MAPPPPPPTATKYFWGDSPEPDEYYASLGLRHAEAYFQSPCGRLFTHSFHPLSAASDGDV

61 KGVVFMSHGYGSDSSWMFQNIAISYARWGYAVFCADLLGHGRSDVRGYLGDTEAVARAA

121 LSFFLSVRRSGAYASLPAFLFGESMGGATTLLAYLRSPPDAGWAGIILSAPLLVFPDDMY

181 PSRVRLFLYGLLFGLADTWAVMPDKRMVGRSIRDPAKLRVIASNPRLYRGSPRVGTMREL

241 ARVTALLRESFGEVAAPFLVVHGTDDGVTSPEGSRMLYERAASEDKSLILYDGMYHSLIQ

301 GESDENRDRVLADMRAWIDERVRRYGAGAGAAAADGHAEAPAA

Eucalyptus grandis predicted protein mRNA. Eucgr.F02557.1
                                                    SEQ ID NO: 15
  1 ttctgggggc acatgccgga ggatgagtac tacgcgtcgc aagggtgcg 51 caactcccag tcctacttcg agaccccaaa cggcaagctc ttcacgcaga 101 gcttccttcc cttggatcag gaagtcaagg cctcggtcta catgacccac 151 ggctacggat ccgacaccgg ctggctcttc cagaagatct gcatcaactt 201 cgccacctgg ggctacgccg tcttcgccgc cgatctcctc ggccacggcc 251 gctccgacgg cctccgttgc tacatgggtg acatggagaa gatcgctgcc 301 acctccgtat cgttcttcac ccacgtccgc aagagcgagc cctacaagga 351 cctgccggcc ttcctgttcg gcgagtccat gggcggggcg acgacaatgc 401 tgatgtactt ccaatccgag cccgacgcat ggacgggatt gatcttctcg 451 gcgccgctct tcgtgatccc ggagaacatg aagcccagca aggtacggct 501 gttcctctac ggcatgctct tcggggtcgc cgacacgtgg gcgagcatgc 551 cggacaacaa gatggtgggg aaggccatca aggaccccga aagctcaag 601 atcatcgcgt cgaacccgcg gaggtacacg ggcaagccga gggtcggcac 651 gatgagggag atcgcccggg tgtgccagta catacaggac aacttcgcca 701 gggtgagcgc cccgttcctg acggtccacg ggacgtcgga cggggtcacg 751 tgccccacct cgtcgcagct cctgtacgag aaggcgtcca gctcggacaa 801 gaccctgaag ctgtacgacg ggatgtacca ctcgctgatc caggggagc
```

```
851 ccgacgagaa cgccgaccgg gtgttgggcg acatgaggga gtggatcgac 901 gagcgggtcg cgaggtacgg gccgaagatc gcc
```

The protein encoded by this sequence is provided below as SEQ ID NO:16.

```
Eucalyptus grandis predicted protein. Eucgr.F02557.1
                                                    SEQ ID NO: 16
   1    FWGHMPEDEY YASQGVRNSQ SYFETPNGKL FTQSFLPLDQ EVKASVYMTH

51    GYGSDTGWLF QKICINFATW GYAVFAADLL GHGRSDGLRC YMGDMEKIAA

101    TSVSFFTHVR KSEPYKDLPA FLFGESMGGA TTMLMYFQSE PDAWTGLIFS

151    APLFVIPENM KPSKVRLFLY GMLFGVADTW ASMPDNKMVG KAIKDPEKLK

201    IIASNPRRYT GKPRVGTMRE IARVCQYIQD NFARVSAPFL TVHGTSDGVT

251    CPTSSQLLYE KASSSDKTLK LYDGMYHSLI QGEPDENADR VLGDMREWID

301    ERVARYGPKI A
```

```
Panicum virgatum predicted protein mRNA. Pavirv0007801m.1
                                                    SEQ ID NO: 17
   1    accaagtact tctggggcga cacccccgag cccgacgagt actacgccgc 51    gcaggggctc cggcacgccg agtcctactt ccagtcccct cacggccgcc 101    tcttcaccca cgccttccac ccgctcgccg gcgacgtcaa gggcgtcgtc 151    ttcatgaccc acggctacgg ttccgactcc tcgtggctct tccagaccgc 201    cgccatcagc tacgcgcgct gggggtacgc cgtcttctgc gccgacctcc 251    tcggccacgg ccgctccgac ggcctccgcg ggtacgtcgg cgacatggag 301    gccgccgccg cggcgtccct cgctttcttc ctctccgtgc gcgccagcgc 351    ggcgtacgcc gcgctcccgg cgttcctgtt cggcgagtcc atgggcggcg 401    ccgccacgct gctcatgtac ctccgctccc cgccgtccgc gcgctggacg 451    gggctcgtgc tctcggcgcc gctcctcgtc atccccgacg gcatgtaccc 501    gtcccgcctc cgcctcttcc tgtacggcct cctcttcggc ctcgccgaca 551    cctgggccgt gctcccggac aagaggatgg tggggaaggc gatcaaggac 601    cccgacaagc tgcggcttat cgcgtccaac ccgctcggct accgcggcgc 651    gccgcgggtg ggcacgatgc gggagctggt ccgcgtgacg gatctgctgc 701    gggagagcct cggggaggtg gcggcgccgt tcctcgccgt gcacgggacg 751    gacgacggcg tgacctcgcc ggaggggtcc aggatgctgt acgagcgcgc 801    gagcagcgag gacaaggagc tcatcctgta cgagggatg taccactcgc 851    tcatccaggg ggagcccgac gagaaccgcg accgcgtgct cgccgacatg 901    cgcaggtgga tcgacgagcg cgtgcgccgc tac
```

The protein encoded by this sequence is provided below as SEQ ID NO:18.

```
Panicum virgatum predicted protein. Pavirv0007801m.1
                                                    SEQ ID NO: 18
   1    TKYFWGDTPE PDEYYAAQGL RHAESYFQSP HGRLFTHAFH PLAGDVKGVV

51    FMTHGYGSDS SWLFQTAAIS YARWGYAVFC ADLLGHGRSD GLRGYVGDME

101    AAAASLAFF LSVRASAAYA ALPAFLFGES MGGAATLLMY LRSPPSARWT

151    GLVLSAPLLV IPDGMYPSRL RLFLYGLLFG LADTWAVLPD KRMVGKAIKD
```

```
201  PDKLRLIASN PLGYRGAPRV GTMRELVRVT DLLRESLGEV AAPFLAVHGT

251  DDGVTSPEGS RMLYERASSE DKELILYEGM YHSLIQGEPD ENRDRVLADM

301  RRWIDERVRR Y
```

As such, it should be understood that this disclosure encompasses modified plants other than modified *Arabidopsis* species, exhibiting modulated function, activity and/or expression of a gene comprising a sequence being functionally similar to or having a degree of homology or identity with, SEQ ID NO:1 or a fragment thereof and/or modulated expression, function and/or activity of a protein or peptide comprising a sequence having a degree of homology or identity with SEQ ID NO:2 or a fragment thereof. For example, the disclosure provides modified plants exhibiting modulated expression, function and/or activity of a gene comprising a sequence selected from the group consisting of the sequences provided by SEQ ID NOS:3; 5; 7; 9; 11, 13, 15 and 17. Additionally or alternatively, the disclosure may relate to modified plants exhibiting modulated function, activity and/or expression of a protein or peptide comprising a sequence selected from the group consisting of the sequences provided by SEQ ID NOS:4, 6, 8, 10, 12, 14, 16 and 18.

It should be understood that the terms "functionally similar" or "functional equivalent" means a protein, which exhibits esterase and/or lysophospholipase 2 like activity or activity which is characteristic of an esterase or lysophospholipase 2. As such, a functionally similar or functionally equivalent esterase and/or lysophospholipase 2 gene may encode a protein exhibiting esterase and/or lysophospholipase 2 like activity or activity which is characteristic of an esterase or a lysophospholipase 2.

The disclosure may relate to modified *Populus trichocarpa*, *Vitis vinifera*, *Glycine max*, *Medicago truncatula*, *Oryza sativa*, *Eucalyptus grandis* and/or *Panicum virgatum* each exhibiting modulated expression of gene exhibiting a degree of homology/identity to or with the *Arabidopsis thaliana* lysophospholipase 2 gene (designated LysoPL2) as described above.

A modified *Populus trichocarpa* may exhibit modulated expression, function and/or activity of a gene encoded by SEQ ID NOS:3 or 5 (encoding the proteins of SEQ ID NOS:4 and 6 respectively).

A modified *Vitis vinifera* may exhibit modulated expression, function and/or activity of a gene encoded by SEQ ID NO:7 (encoding the protein of SEQ ID NO:8).

A modified *Glycine max* may exhibit modulated expression, function and/or activity of a gene encoded by SEQ ID NO:11 (encoding the protein of SEQ ID NO:12).

A modified *Medicago truncatula* may exhibit modulated expression, function and/or activity of a gene encoded by SEQ ID NO:9 (encoding the protein of SEQ ID NO:10).

A modified *Oryza sativa* may exhibit modulated expression, function and/or activity of a gene encoded by SEQ ID NO:13 (encoding the protein of SEQ ID NO:14).

A modified *Eucalyptus grandis* may exhibit modulated expression, function and/or activity of a gene encoded by SEQ ID NO:15 (encoding the protein of SEQ ID NO:16).

A modified *Panicum virgatum* may exhibit modulated expression, function and/or activity of a gene encoded by SEQ ID NO:17 (encoding the protein of SEQ ID NO:18).

The term "degree of homology/identity" may encompass nucleic acid and/or amino acid sequences which exhibit at least about 30%, 40%, 50%, 60%, 65%, 70%, 75%, 80%, 85%, 90%, 91%, 92%, 93%, 94%, 95%, 96%, 97%, 98% or 99% homology or identity with SEQ ID NOS:1 or 2 (or any of the sequences given as SEQ ID NOS:3-18 herein), or fragments thereof.

The degree of (or percentage) "homology" between two or more (amino acid or nucleic acid) sequences may be determined by aligning the sequences and determining the number of aligned residues, which are identical, and adding this to the number of residues that are not identical but that differ by redundant nucleotide substitutions, the redundant nucleotide substitution has no effect upon the amino acid encoded by a particular codon or conservative amino acid substitutions. The combined total is then divided by the total number of residues compared and the resulting figure is multiplied by 100; this yields the percentage homology between aligned sequences.

A degree of (or percentage) "identity" between two or more (amino acid or nucleic acid) sequences may also be determined by aligning the sequences and ascertaining the number of exact residue matches between the aligned sequences and dividing this number by the number of total residues compared; multiplying the resultant figure by 100 would yield the percentage identity between the sequences.

Proteins and/or peptides exhibiting homology or identity to/with a lysophospholipase protein or to/with a protein/peptide encoded by SEQ ID NO:2 or a fragment thereof (or 4, 6, 8, 10, 12, 14, 16 or 18 or a fragment thereof) may comprise one or more conservative amino acid substitutions. One of skill in this field will understand that a conservative substitution, represents one or more residues, which are different from the residues present in a reference sequence (for example, SEQ ID NOS:2, 4, 6, 8, 10, 12, 14, 16 or 18 or a wild-type esterase and/or lysophospholipase protein sequence), but which do not substantially alter the physicochemical properties and/or structure or function of the protein.

As is well known in the art, the degeneracy of the genetic code permits substitution of one or more bases in a codon without changing the encoded primary amino acid sequence. Consequently, although the sequences described in this application (for example, SEQ ID NOS:1, 3, 5, 7, 9, 11, 13, 15 or 17) are known to encode esterase and/or lysophospholipase enzymes, the degeneracy of the nucleic acid code may be exploited to yield variant nucleic acid sequences, which encode the same primary amino acid sequences.

It should be understood that fragments of any of the sequences described herein (for example, those designated SEQ ID NOS:1-18) may comprise any size from about 10 residues to (n−1) residues, where "n" is the total number of residues in the complete or native amino acid/nucleic acid sequence.

By way of example, fragments of SEQ ID NO:1 may comprise short oligomeric sequences comprising 30-1418 nucleic acids. In one embodiment, the fragments may comprise 60, 90, 120, 150, 180, 210, 300, 390, 480, 570, 690, 780, 810, 900, 990, 1080, 1170, 1260, 1350 or 1410 nucleotides or consecutive nucleotides of SEQ ID NO:1. Similarly, fragments of SEQ ID NO:2, may comprise about 10 to about 331 amino acids, for example, 10, 20, 30, 40, 50, 60, 70, 80, 90, 100, 110, 120, 130, 140, 150, 160, 170, 180, 190, 200, 210, 220, 230, 240, 250, 260, 270, 300, 310, 320 or 330 amino acids (for example, contiguous amino acids) of SEQ ID NO:2.

In view of the above, one embodiment of this disclosure provides a plant exhibiting modulated expression, function and/or activity of one or more lipase/esterase/thioesterase family gene(s), the one or more lipase/esterase/thioesterase family gene(s) being selected from the group consisting of:

(i) a gene encoded by SEQ ID NO:1 (or a fragment thereof);

(ii) a gene having a degree of identity or homology with SEQ ID NO:1 (or a fragment thereof);

(iii) a gene encoded by any of the sequences designated SEQ ID NOS:3, 5, 7, 9, 11, 13, 15 or 17 or a fragment thereof;

(iv) a gene having a degree of identity or homology with and of SEQ ID NOS:3, 5, 7, 9, 11, 13, 15 or 17; and (v) a gene encoding a protein functionally similar or equivalent to a protein encoded by any of the sequences designated SEQ ID NOS:1, 3, 5, 7, 9, 11, 13, 15 or 17;

wherein the plant comprises modified lignin.

Additionally or alternatively, an embodiment of this disclosure provides a plant exhibiting modulated expression, function and/or activity of one or more esterase/lysophospholipase enzyme(s), the esterase/lysophospholipase enzyme(s) being selected from the group consisting of:

(i) an esterase/lipophospholipase enzyme encoded by SEQ ID NO:2 (or a fragment thereof);

(ii) an esterase/lipophospholipase enzyme encoded by a protein having a degree of homology/identity with SEQ ID NO:2 (or a fragment thereof);

(iii) an esterase/lipophospholipase enzyme encoded by a protein having a sequence corresponding to a sequence designated SEQ ID NOS:4, 6, 8, 10, 12, 14, 16 or 18 or a fragment thereof;

(iv) an esterase/lipophospholipase enzyme encoded by a sequence having a degree of homogy/identity with any of SEQ ID NOS.4, 6, 8, 10, 12, 14, 16 or 18; and (v) an esterase/lipophospholipase enzyme functionally similar or equivalent to a lipophospholipase enzyme encoded by any of SEQ ID NOS:2, 4, 6, 8, 10, 12, 14, 16 or 18;

wherein the plant comprises modified lignin.

The plants provided by this disclosure may be genetically modified so as to exhibit modulated expression of one or more lipase/esterase/thioesterase family gene(s) and/or a modulated level of esterase/lysophospholipase expression.

As such, this disclosure encompasses plants which comprise modified lipase/esterase/thioesterase family gene sequence(s). In the context of this disclosure, a "modified sequence" may comprise one or more mutations such as, for example, one or more nucleic acid or amino acid additions, deletions, substitutions and/or inversions (collectively referred to as modifications), which modifications affect the level of expression, function and/or activity of a lipase/esterase/thioesterase family gene or a protein encoded thereby. In one embodiment, the one or more mutations of the modified sequences may ablate or reduce the expression of a lipase/esterase/thioesterase family gene and/or the activity and/or function of any lipase/esterase/thioesterase encoded thereby. Such mutations may be collectively referred to as loss-of-function mutations.

It should be understood that the level of expression of a lipase/esterase/thioesterase family gene or a protein encoded thereby may be assessed relative to the expression of a corresponding lipase/esterase/thioesterase family gene or a protein encoded thereby in a control plant.

One of skill will appreciate that there are many ways of introducing genetic modifications into plant genomes and all of these techniques apply here. For example, it may be possible exploit random mutagenesis methods such as irradiation, random DNA integration and/or chemical mutagen processes in order to modify lipase/esterase/thioesterase family gene(s) so as to provide plants exhibiting a modified lignin content. Additionally or alternatively, lipase/esterase/thioesterase family gene(s) may be modified or mutated by techniques, which may include, for example, *Agrobacterium*-mediated transformation, biolistics, site or oligonucleotide-directed mutagenesis, oligonucleotide-directed repair, zinc finger nuclease technology, TALE-based hybrid nucleases, and site-specific recombination.

In one embodiment, a plant may be modified using any of the techniques described above, such that expression of lipase/esterase/thioesterase family gene/protein(s) is/are partially or completely ablated, such plants may exhibit a modified or altered lignin.

However, one of skill will appreciate that in some cases a degree of lignin production may be desirable and modified plants of this disclosure may be further modified by the introduction of expression vectors, which encode one or more expressible lipase/esterase/thioesterase family gene sequences. In one embodiment, the expression vectors may direct reduced expression of one or more functional lipase/esterase/thioesterase family gene(s) leading to reduced expression of lipase/esterase/thioesterase family protein(s) in transformed plant tissues (again "reduced" expression of a lipase/esterase/thioesterase family gene/protein(s) may be assessed relative to the levels of expressions observed in a control plant). Alternatively, a vector may encode (or direct the expression of) one or more fully or partially functional lipase/esterase/thioesterase family gene/protein(s) in a wild-type plant, or in a plant that does not express the endogenous lipase/esterase/thioesterase gene or protein.

In other embodiments, wild-type or unmodified plants may be modified by the introduction of one or more vectors, which encode one or more expressible lipase/esterase/thioesterase family gene/protein(s). The introduction of such vectors may trigger co-suppression of endogenous lipase/esterase/thioesterase family gene/protein(s) or may (in some cases) bring about an increase in lignin production.

In other embodiments, the modified plants provided by this disclosure may comprise one or more nucleic acid sequences, which are complementary to a sequence provided by this disclosure, for example, a sequence derived from SEQ ID NO:1 (or SEQ ID NOS:3, 5, 7, 9, 11, 13, 15 or 17). Such sequences may be known as sense or antisense sequences. Antisense oligonucleotides sequences may comprise DNA that gives rise to a variety of small/short interfering and/or silencing RNAs, such molecules being referred to hereinafter as siRNA.

In one embodiment, the modified plants of this disclosure may comprise one or more inverted repeat elements designed to silence one or more lipase/esterase/thioesterase family gene sequences. One of skill will appreciate that an inverted repeat element may comprise an antisense sequence and sense sequence separated by a hairpin structure. Such elements may be introduced into plants via vectors which encode one or inverted repeat elements.

Antisense oligonucleotides sequences for use in this disclosure (such as those designed to modulate the expression, function and/or activity of a sequence of SEQ ID NO:1) may be comprised within a nucleic acid construct operably linked to, for example, a suitable promoter sequence. In one embodiment, a construct of this disclosure may comprise a constitutive or tissue specific promoter sequence or a tissue, cell, seed or organelle specific promoter.

In view of the above, the disclosure extends to plants comprising a modified lignin content and one or more antisense sequences or inverted hairpin constructs, which affect the expression, function and/or activity of one or more lipase/esterase/thioesterase family gene(s). In one embodiment, the modified plants of this disclosure may comprise (exogenous) nucleic acid sequences, which encode sections or parts of one or more lipase/esterase/thioesterase family gene(s). For example, such sequences may comprise approximately 200 bp-1 kb of a lipase/esterase/thioesterase family gene sequence and be introduced as part of an expression cassette or vector, such as, for example, T-DNA (for Agrobacterium-mediated transformation) or by biolistics.

This disclosure extends to plants generated by new breeding techniques such as Zinc finger nuclease (ZFN) technology (ZFN-1, ZFN-2 and ZFN-3), Oligonucleotide directed mutagenesis (ODM), Cisgenesis and intragenesis, RNA-dependent DNA methylation (RdDM) [3, 12].

As mentioned above, the modified lignin of the plants described herein, ensures sugars can be more efficiently released. As such, this disclosure further provides a method of increasing the level or availability of one or more carbohydrate(s) in a plant, the method comprising the steps of modulating the expression of one or more lipase/esterase/thioesterase family gene(s) and/or the expression, function and/or activity of one or more lipase/esterase/thioesterase family protein(s).

In one embodiment, the one or more carbohydrates are fermentable carbohydrates such as, for example, cellulose, hemicelluloses, or glucose. In a further embodiment, the plant may be a plant grown as a biofuel crop.

In a further aspect, there is provided a plant or plant material for use in methods which require release (or exploitation of) carbohydrates from plants, wherein the plant is a plant according to the first aspect of this disclosure and/or the plant material is derived from a modified plant provided by the first aspect of this disclosure.

In one embodiment, the method is, for example, a biorefinery method or a method of biofuel, animal feed, bioplastic, chemical, pulp or paper production.

In one embodiment, there is provided a modified plant of the first aspect of this disclosure, or material derived therefrom, for use in methods of producing biofuels.

In a further aspect, the disclosure provides a method of producing a biofuel, the method comprising the steps of obtaining material from a plant, according to the first aspect of this disclosure, and subjecting the material (or carbohydrates thereof) to a fermentation protocol. In one embodiment, the biofuel is a bioethanol.

In another aspect, the disclosure provides a method of modifying the lignin content of a plant, the method comprising the step of modifying the expression of one or more lipase/esterase/thioesterase family gene(s) and/or the expression, function and/or activity of a lipase/esterase/thioesterase family protein(s). In one embodiment, the modified lignin content comprises a reduced lignin content and/or lignin having an altered composition and/or structure.

In a further aspect, the disclosure provides a biofuel, animal feed, bioplastic, chemical, pulp or paper produced by a method exploiting material (biomass) derived from the modified plants described herein.

It should be understood that the modified plants provided by this disclosure may comprise one or more other modifications which affect lignin biosynthesis. For example, in addition to exhibiting modulated expression of one or more lipase/esterase/thioesterase family gene, the plants of this disclosure may exhibit modulated expression of one or more other genes involved in lignin biosynthesis.

DETAILED DESCRIPTION

Figure 1B:
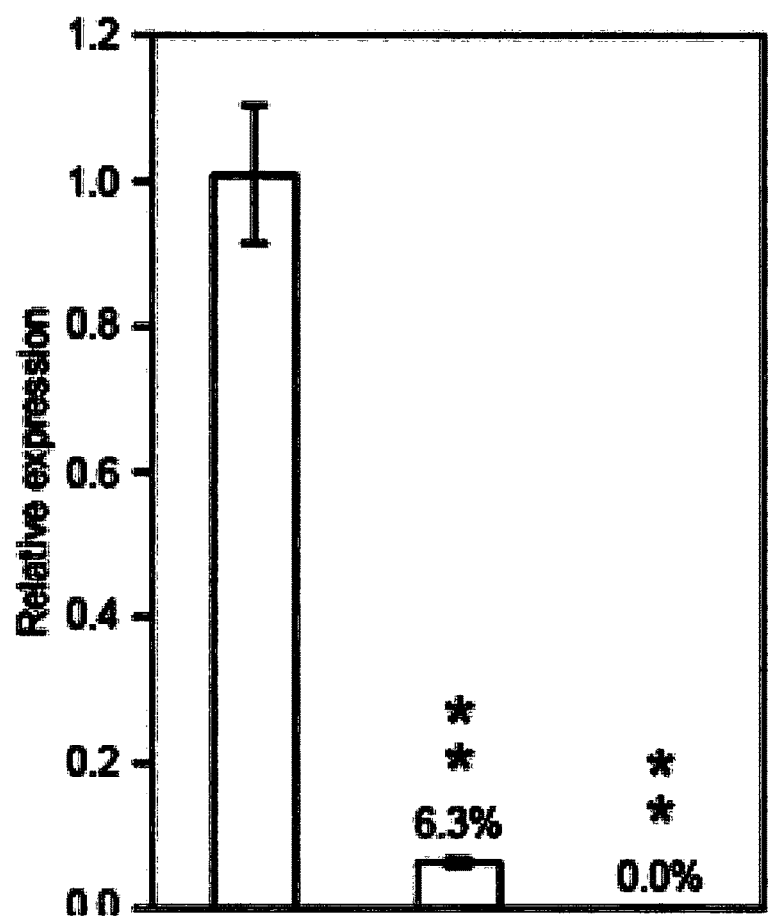

The disclosure will now be described in detail with reference to the following figures which show:

FIGS. 1A and 1B: *Arabidopsis* mutants in AT1G52760 (encoding a lysophospholipase/thiolesterase LysoPL2) have reduced (mutant Mx12_7) or virtually abolished (mutant Gb9) expression of AT1G52760 RNA compared to wild-type Col-0. The gene AT1 G52760 was identified as being tightly co-expressed with lignin biosynthesis genes using methods similar to [6-8]. Levels of AT1G52760 mRNA were estimated by qRT-PCR. **$0.01>p>0.001$.

Figure 2A:
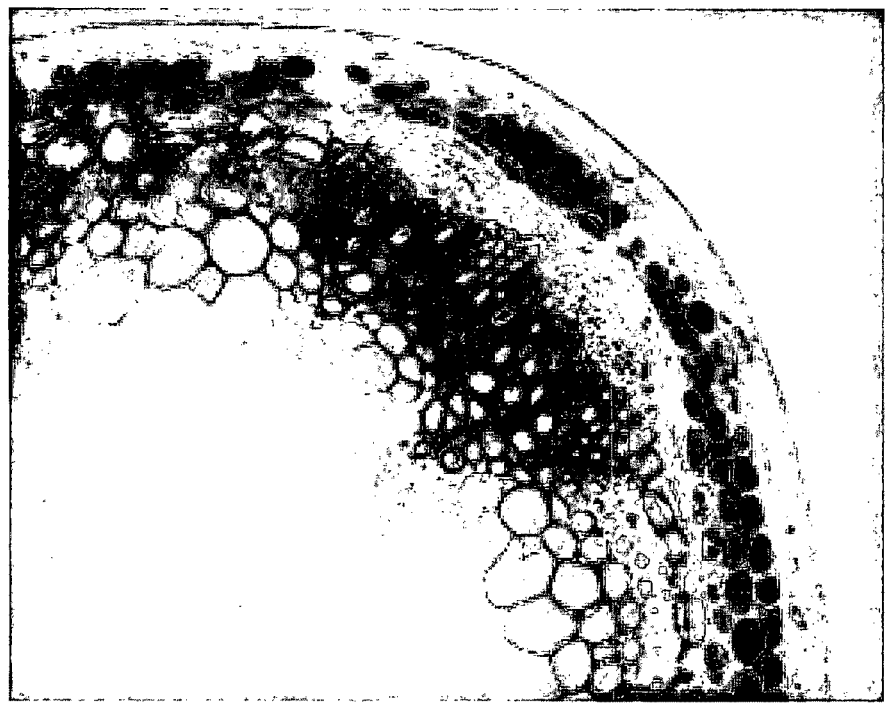

FIG. 2A: Stem cross sections stained with Maule reagent reveal that mutant Gb9 with defective AT1G52760 expression (bottom) shows less red staining in fibres and more irregular shaped xylem vessels compared to wild-type plants (top).

Figure 2A:
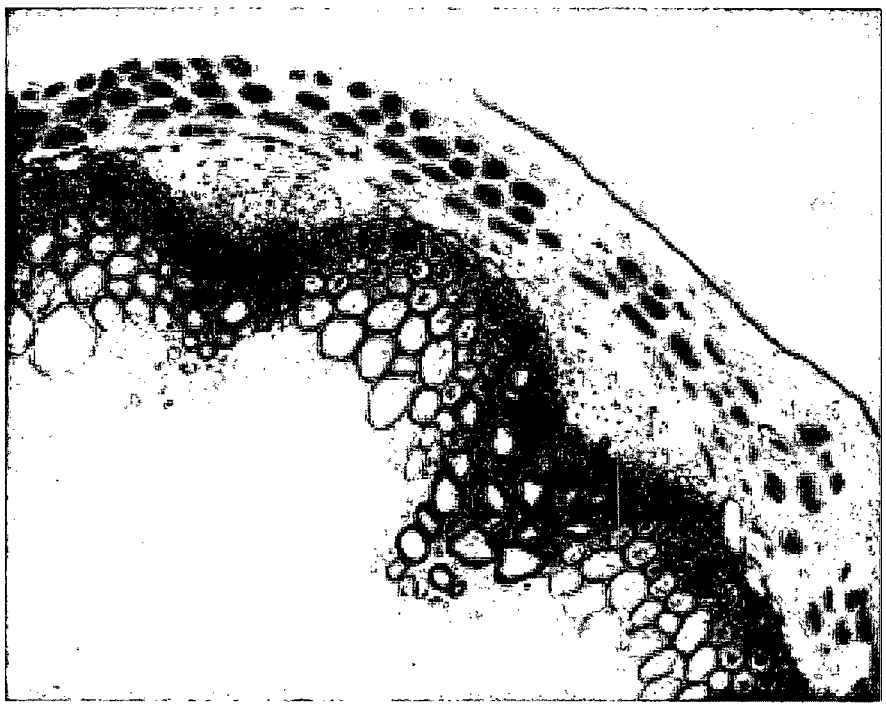
Figure 2B:
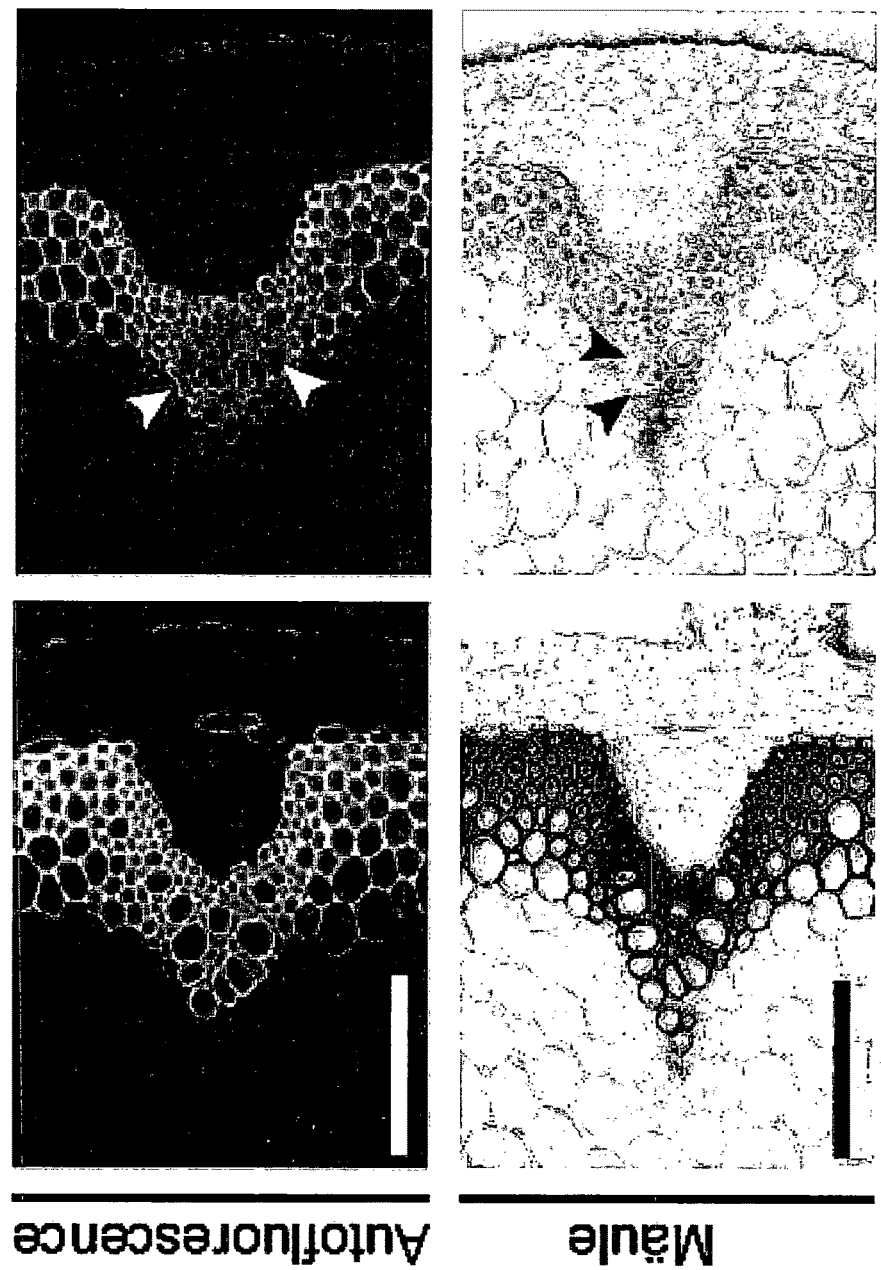

FIG. 2B: Stem cross sections autofluorescence (top) and stained with Maule reagent (bottom) reveal that mutant Gb9 (right-hand side) with defective AT1G52760 expression shows less lignin autofluorescence, less Maule red staining in fibres, and more irregular shaped xylem vessels compared to wild-type plants (left-hand side).

Figure 3A:
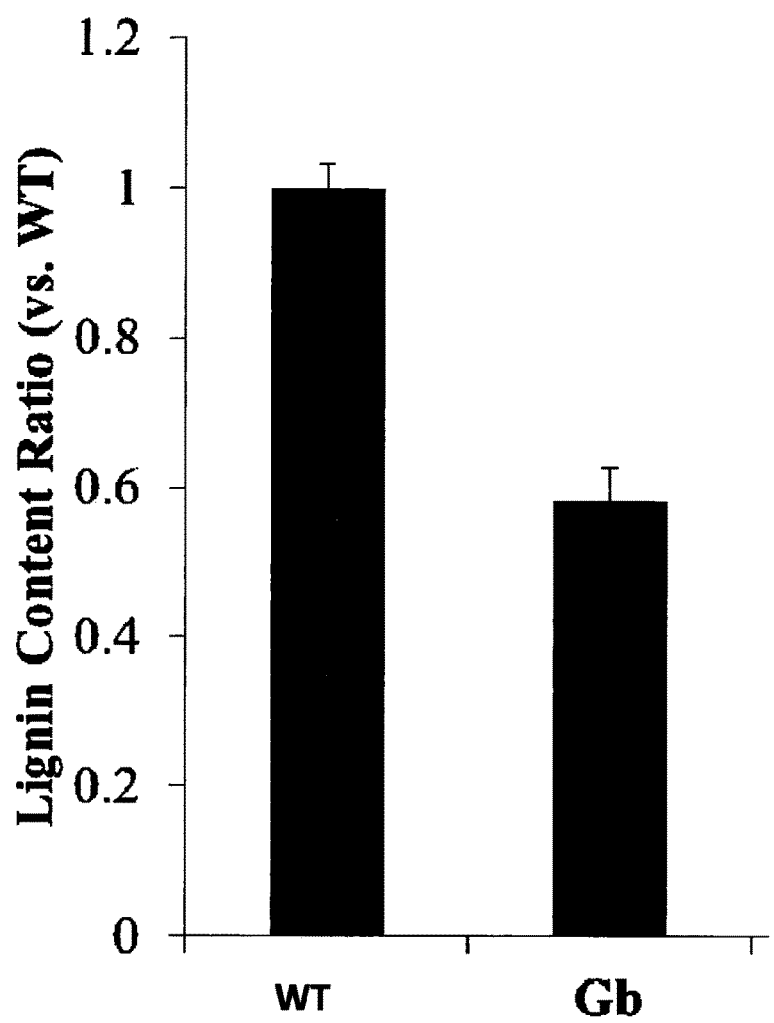

FIGS. 3A-C: *Arabidopsis* mutant Gb9 with defective AT1G52760 expression has reduced lignin, with levels significantly lower than wild-type plants (WT). Lignin was determined by the acetyl bromide method similar to [9]. (C) Shows the altered monomer structure; lignin was determined by the acetyl bromide method similar to [9] and by thioacidolysis to determine H, G and S units.

Figure 4A:
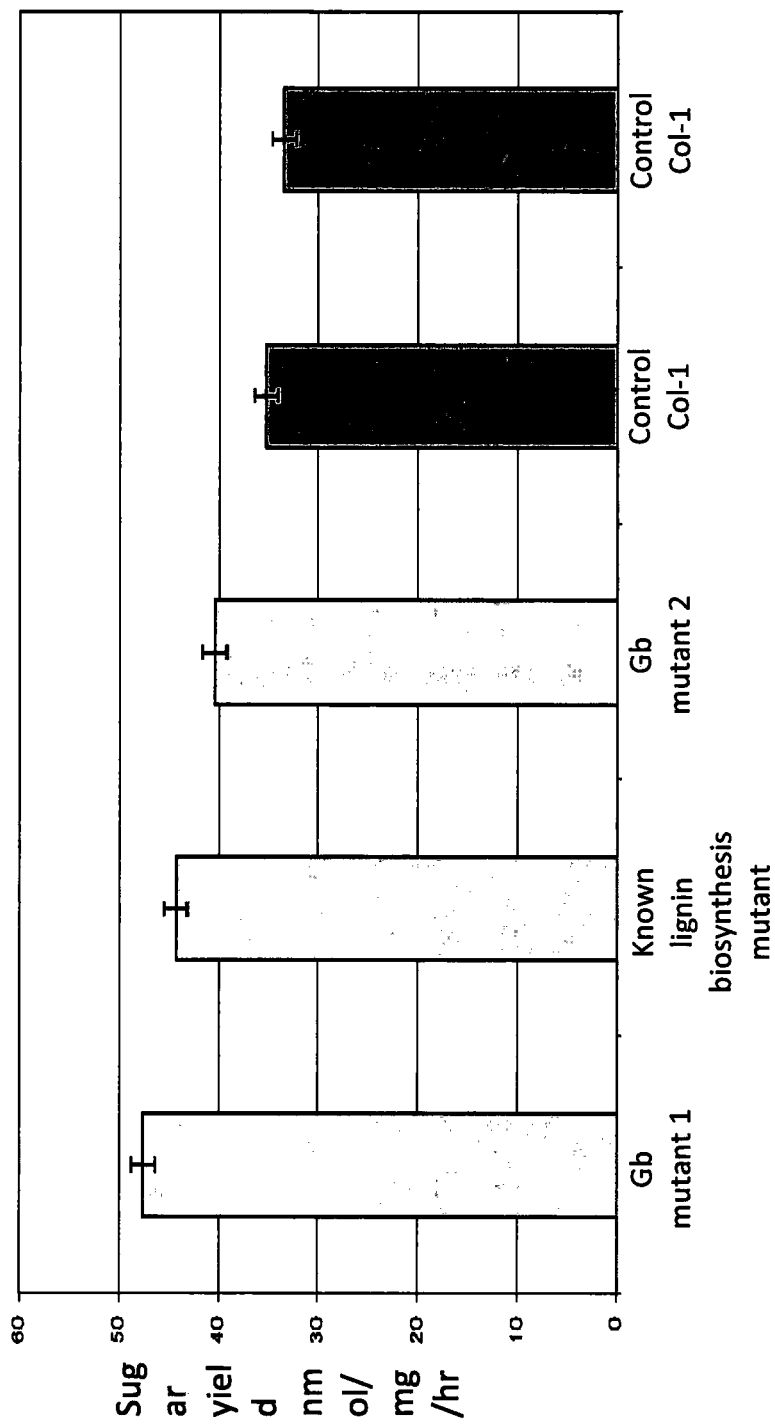

FIG. 4A: *Arabidopsis* mutant Gb9 with defective AT1G52760 expression has increased sugar yield on cell wall saccharification, with levels comparable to known lignin mutants ccr1 and ref3-3, and significantly higher than Col-0 wild-type control plants. Saccharification was determined in a relatively mild assay using methods similar to [10]. Greater improvements in saccharification might be expected under conditions with higher enzyme loading left for longer time.

Figure 4B:
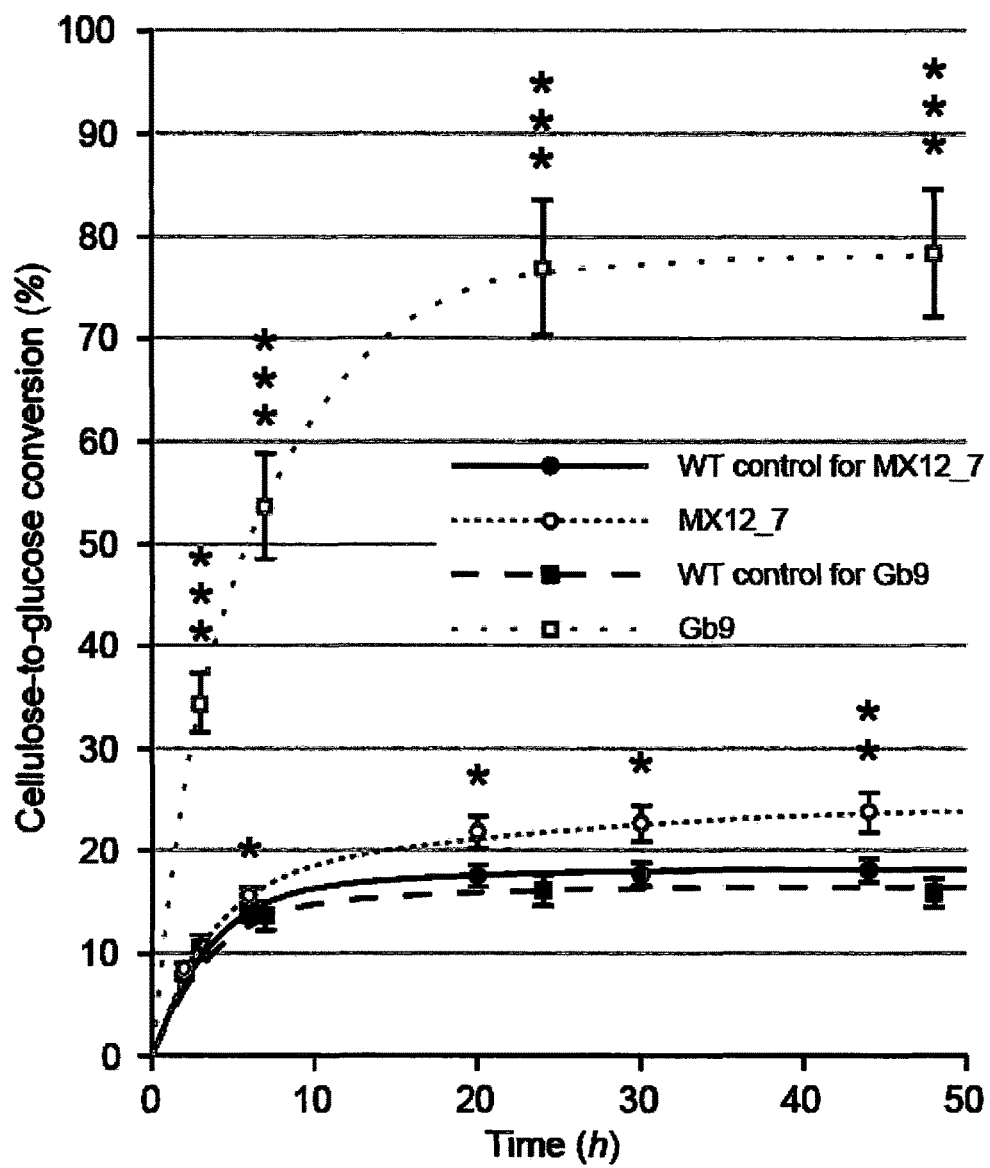

FIG. 4B: *Arabidopsis* mutants Gb9 and Mx12_7 with defective AT1G52760 expression have increased cellulose-to-glucose conversion on cell wall saccharification compared to wild-type plants. Error bars represent the standard error. *$0.05>p>0.01$, $0.01>p>0.001$, *$0.001>p$.

Figure 5A:
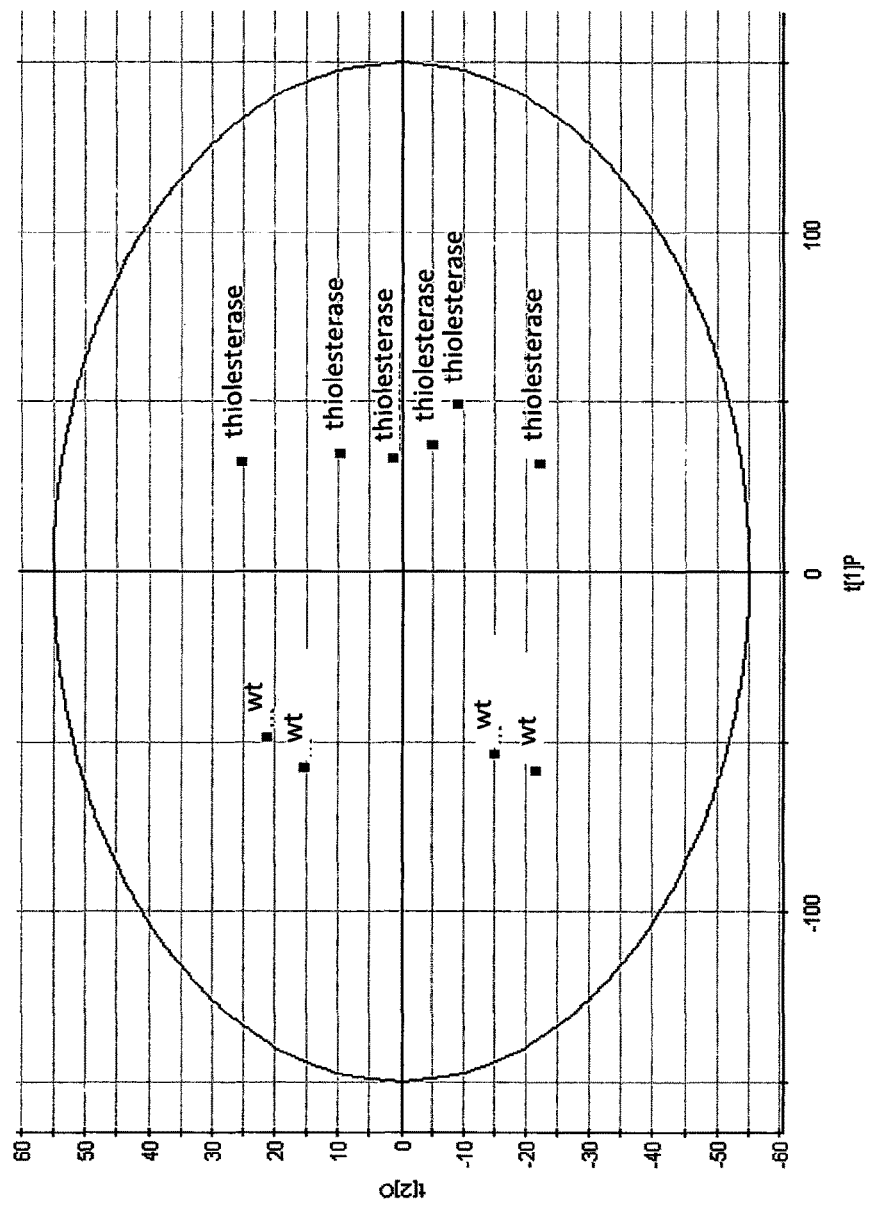
Figure 5B:
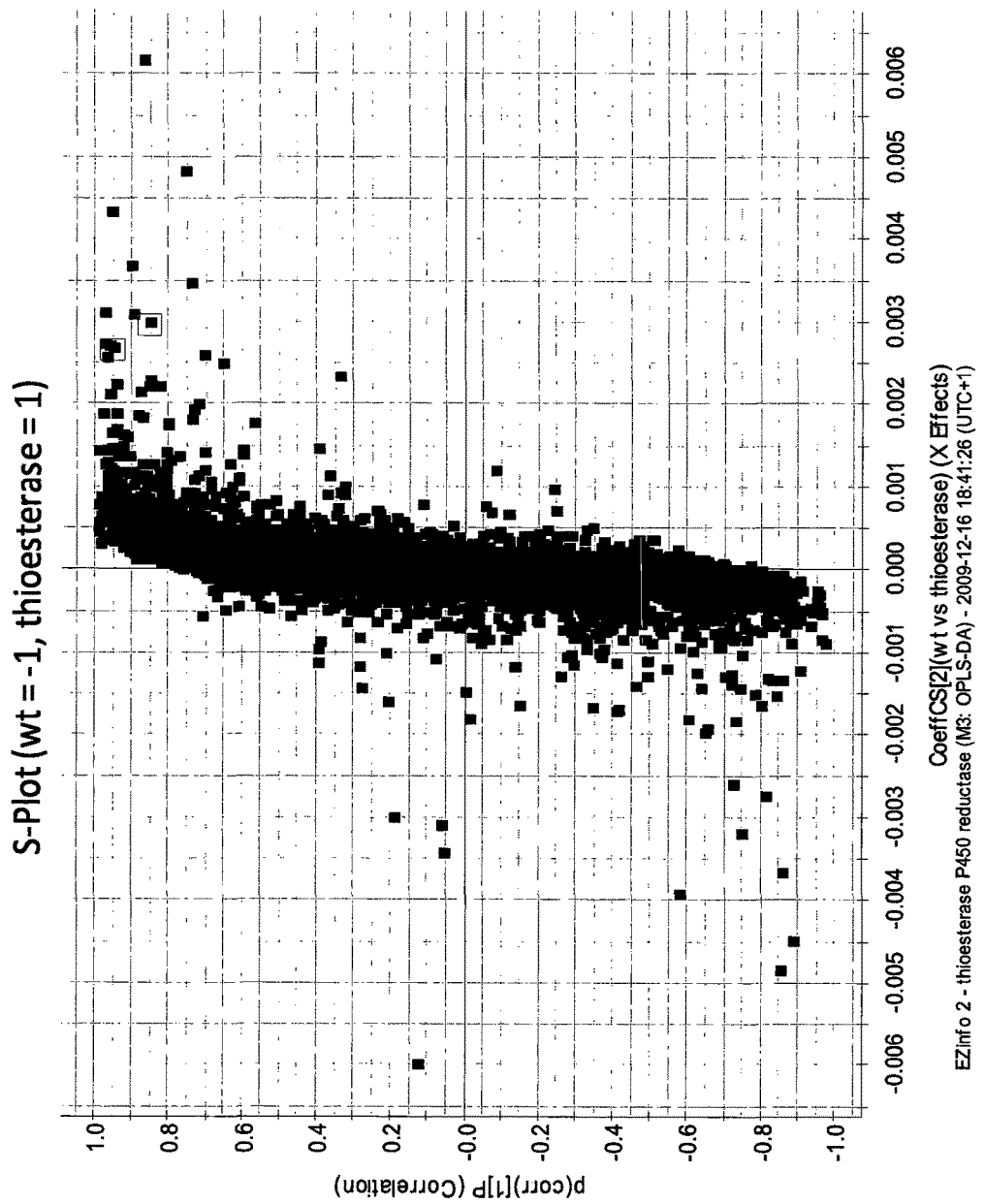
Figure 5C:
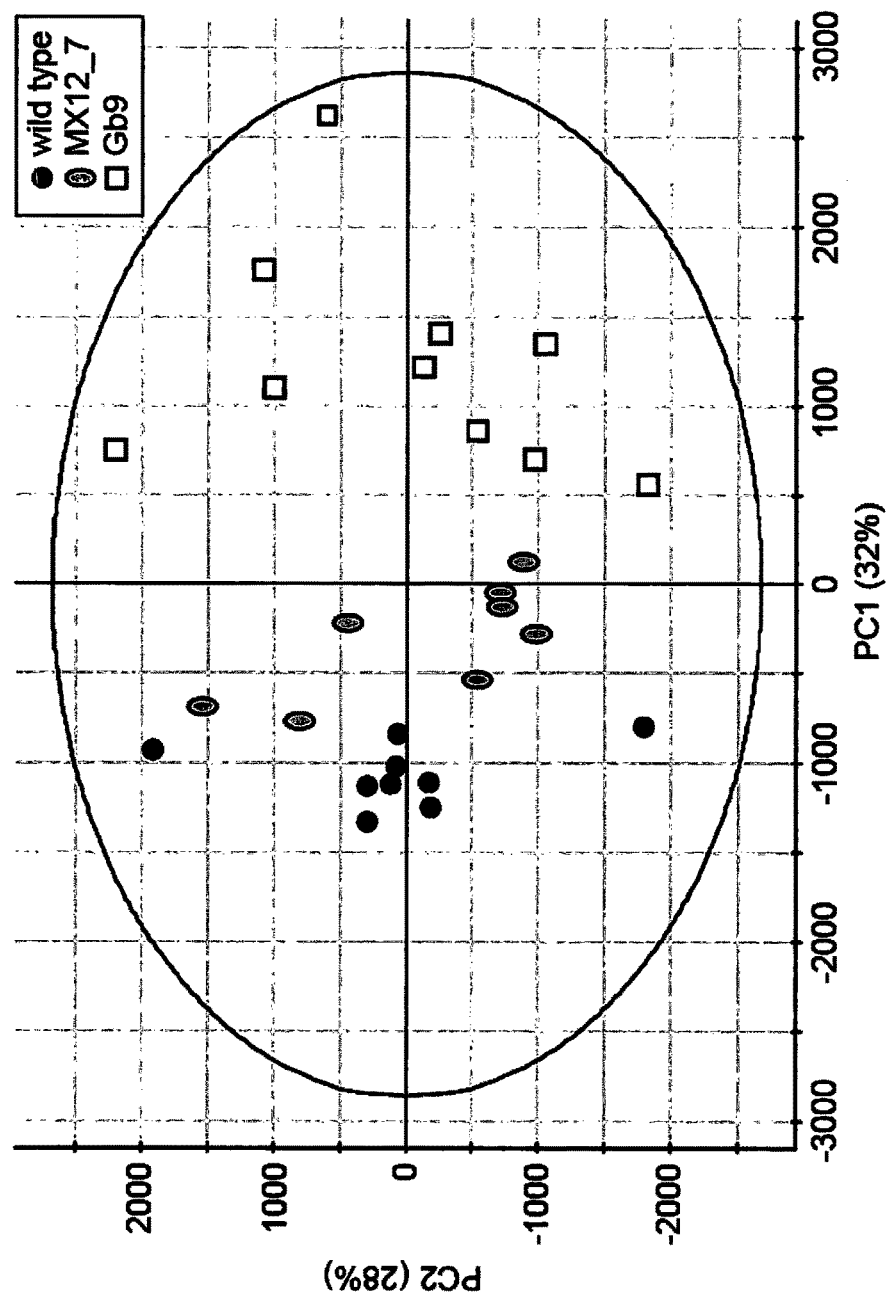

FIGS. 5A-C: Phenolic profiling reveals that there are differences in metabolite accumulation between wild-type (wt) and the lysophospholipase/thioesterase mutants Mx12 7 and Gb9. PCA plots show that the wild-type profiles cluster differently from those of the mutants while an S-plot analysis also confirms that some metabolites accumulate differentially between mutants and wild-type (revealed by outlying dots in the tails of the S-plot).

Figure 6:
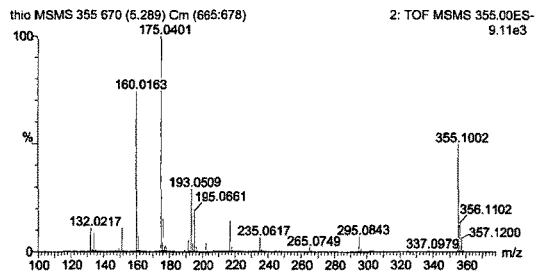
Figure 6:
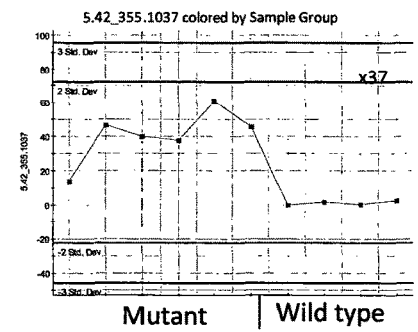
Figure 6:
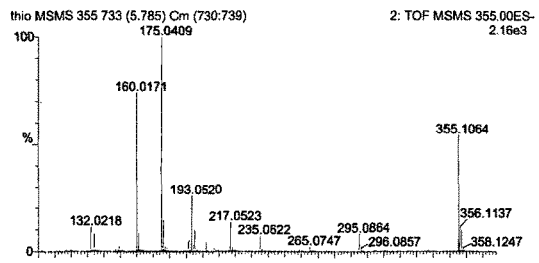
Figure 6:
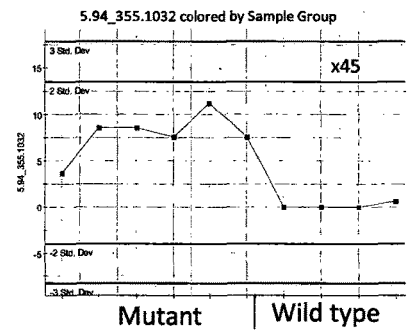
Figure 6:
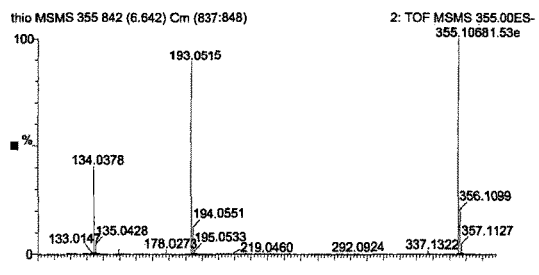
Figure 6:
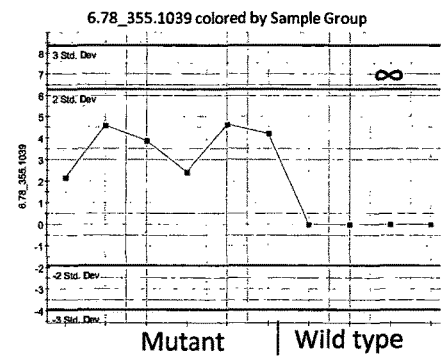

FIG. 6: Differential accumulation of three compounds that are present in different levels in the lysophospholipase/thioesterase mutant and the wild-type is illustrated in the right-hand side column of graphs while the mass spectra of these compounds is shown in the left-hand side column.

Figure 7:
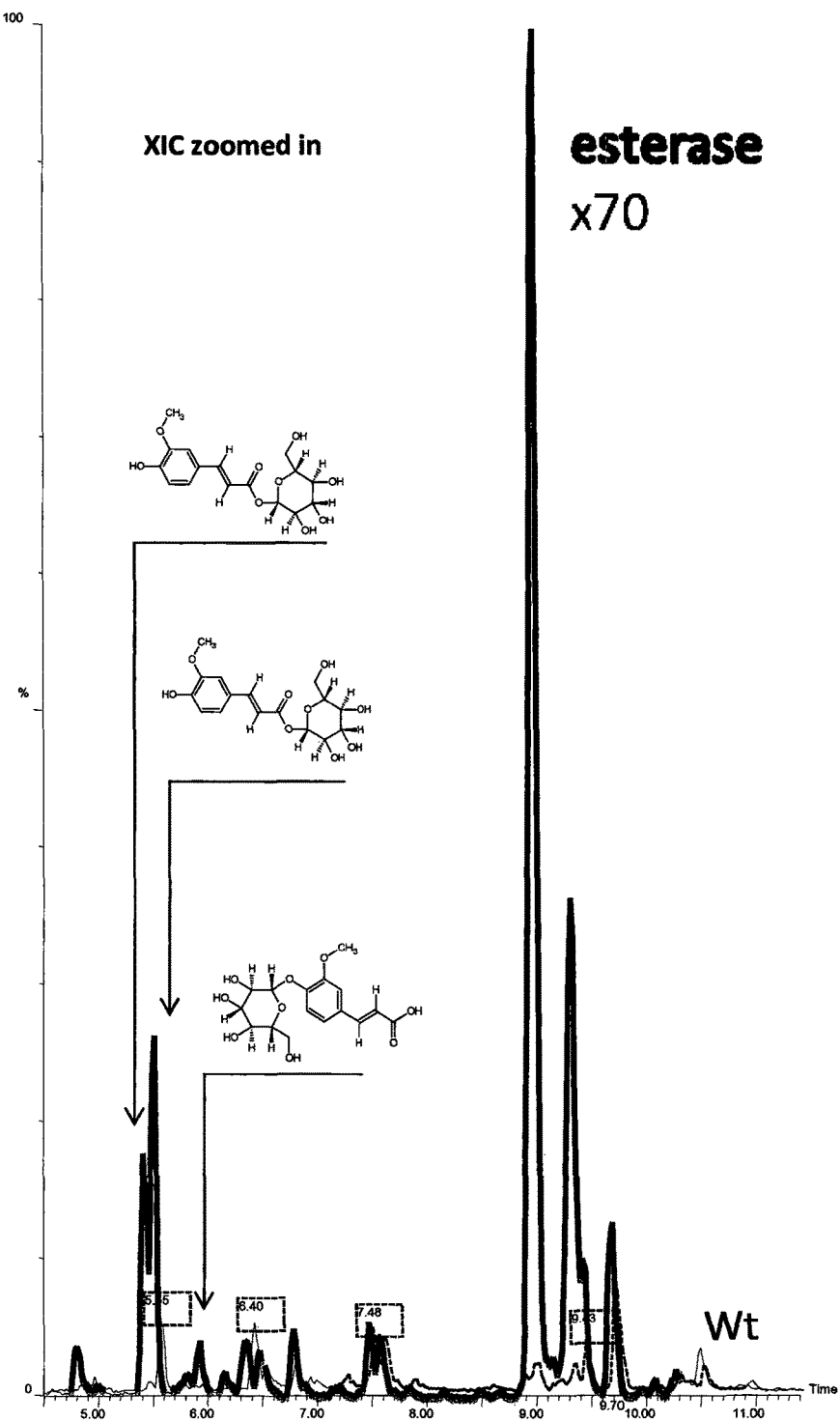

FIG. 7: *Arabidopsis* mutant with defective AT1G52760 expression (green line) has more ferulate esters and glucosides on phenolic profiling than wild-type plants (red line).

Two peaks that accumulate in the thioesterase mutant correspond to ferulate glucose ester and one to ferulic acid glucoside. The peak that accumulates 70-fold is feruloyl malate.

Figure 8:
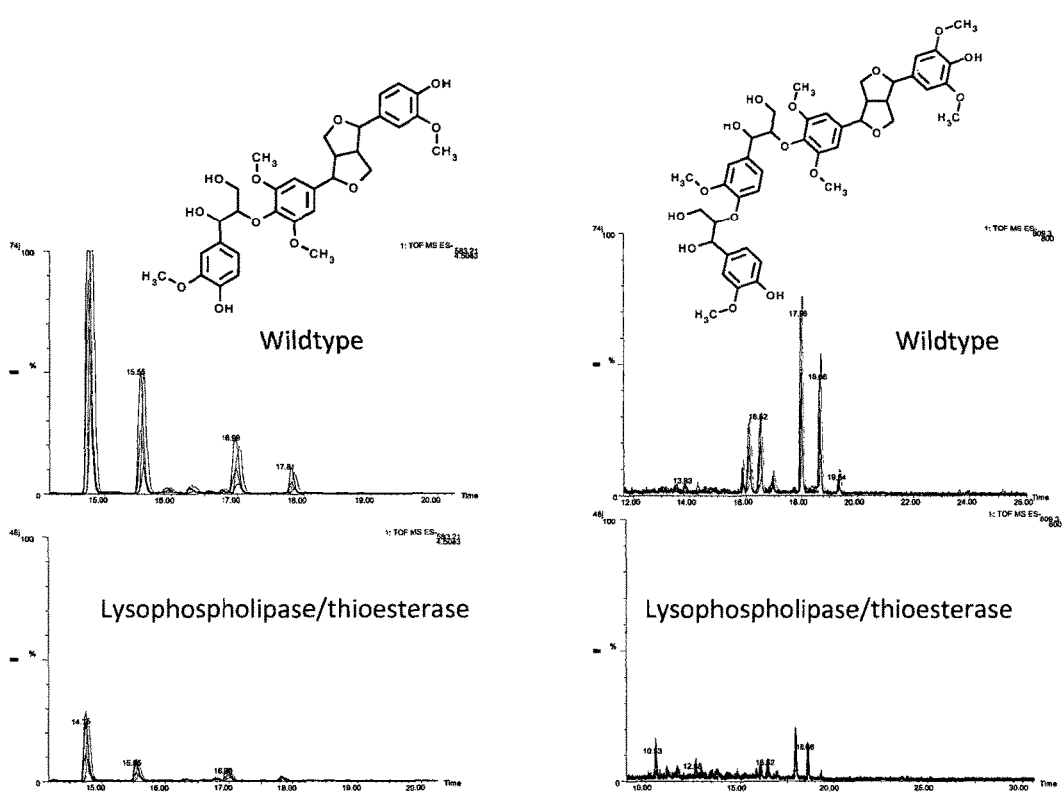

FIG. 8: *Arabidopsis* mutant with defective AT1G52760 expression (green line) has less lignin oligomers than wild-type plants (red line).

Figure 9:
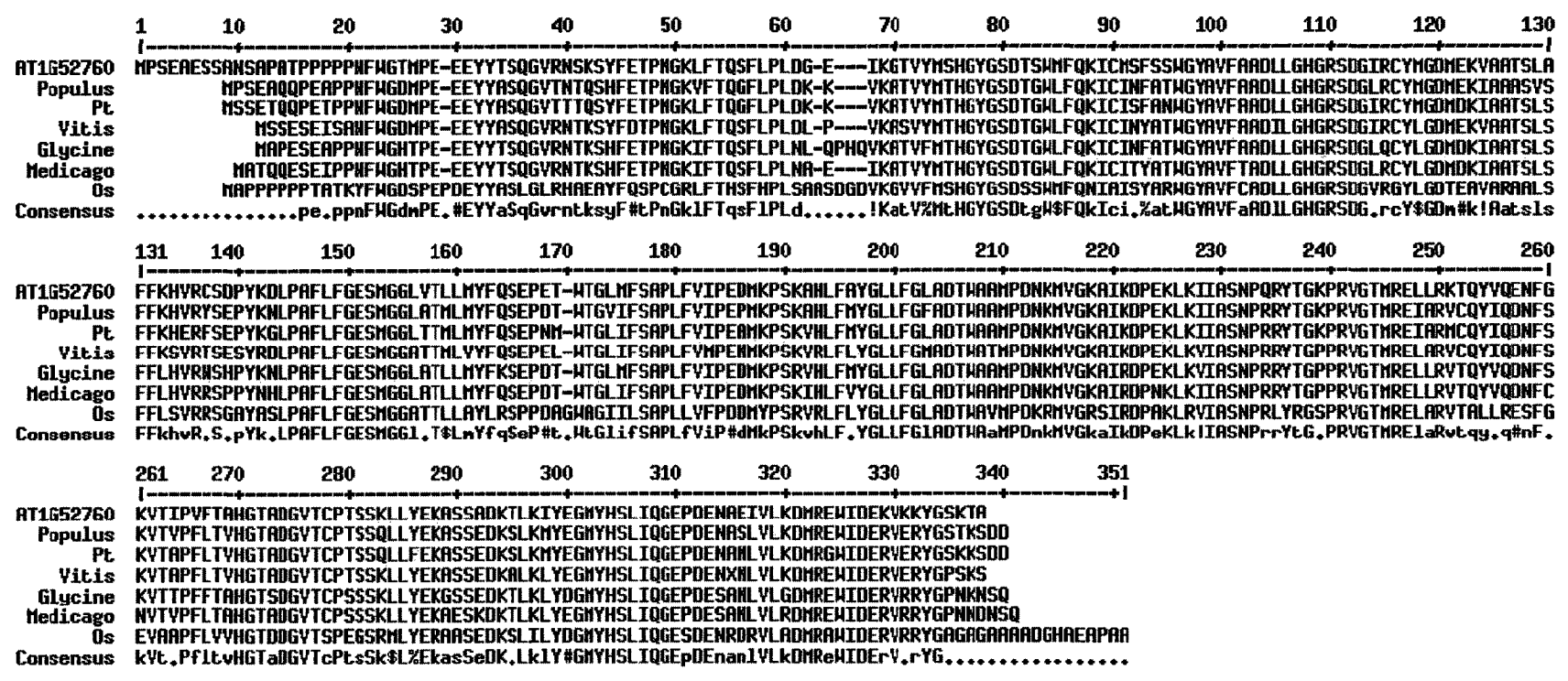

FIG. 9: Multiple alignment of *Arabidopsis* AT1G52760 amino acid sequence and similar sequences from other plant species. AT1G52760 has previously been described as a lysophospholipase 2 (LysoPL2) involved in tolerance to cadmium-induced oxidative stress [11]. No basis for a role in lignin biosynthesis has previously been proposed. (AT1G52760 (SEQ ID NO:2); Populus (SEQ ID NO:4); Pt (SEQ ID NO:6); Vitis (SEQ ID NO:8); Glycine (SEQ ID NO:12); Medicago (SEQ ID NO:10); Os (SEQ ID NO:14))

Materials & Methods

Co-Expression Analysis and Selection of *Arabidopsis* Mutants

A variety of tools [6-8] including ACT and CressExpress were used to search for genes that have similar expression patterns to individual lignin biosynthesis genes. In total, 255 genes were retrieved, with some of them shared between different analyses; 102 of them were chosen for further investigation. To investigate the potential biological function of these genes, we searched the Nottingham Arabidopsis Stock Centre (NASC) for available T-DNA insertion mutants in these genes and obtained 66 homozygous mutants, including two, renamed Gb9 and Mx12-7, that are mutated in AT1G52760, a gene annotated as encoding a lipase/thioesterase enzyme and later described as a lysophospholipase [11] with no known role in lignin biosynthesis. FIG. 1 shows that Mx12-7 retains a very small level of the AT1G52760 lysophospholipase/thioesterase expression while in Gb9, no expression was detected. Expression was quantified by standard QRT-PCR analysis.

Lignin Determinations, Saccharification Analysis, and Phenolic Profiling

Histochemical staining with Maule reagent (which stains S lignin) of transverse stem sections from the Gb9 mutant showed reduced lignin staining and collapsed xylem indicative of a cell wall defect (FIG. 2). Acetyl bromide lignin determinations [9] carried out on *Arabidopsis* mutant Gb9 showed that it has reduced lignin, with levels significantly lower than wild-type plants (FIG. 3). This suggests that the AT1G52760 lysophospholipase plays some unknown role in determining the amount of lignin deposited in *Arabidopsis* and possibly other plants. We subsequently demonstrated a significant improvement in the release of sugar from plant cell walls of the Gb9 mutant (FIG. 4), which releases levels comparable to that of known lignin mutants (ccr1), and significantly higher than the levels released by Col-0 wild-type plants. This saccharification assay is a very mild treatment and does not indicate the maximum possible sugar release from these genotypes but merely reveals differences between them under mild conditions. Saccharification was evaluated by grinding stem material to a fine powder, pretreating it with mild acid (typically 1% H2SO4), washing the residue and subjecting it to enzymic hydrolysis with Novozymes 188 plus Celluclast. Levels of simple reducing sugars released were determined by MBTH detection using methods similar to [10]. These data illustrating improved saccharification of Gb9 suggest that it may be a novel point at which to manipulate lignin biosynthesis to improve sugar release for biofuel production. Phenolic profiling by Ultra-high Pressure Liquid Chromatography (UPLC) of methanol-soluble phenolic compounds revealed that some metabolites accumulate differentially between the wild-type and the lysophospholipase/thioesterase mutant. PCA plots (FIG. 5, top) confirmed that the wild-type profiles differ from those of the mutant, as did an S-plot analysis (FIG. 5, bottom). Dots in the tails of the S-plot designate metabolites that accumulate differentially between mutant and wild-type. The mass spectra of three compounds that accumulate differentially between the lysophospholipase/thioesterase mutant and the wild-type are shown in FIG. 6. Two peaks that accumulate in the mutant correspond to ferulate glucose ester and one to ferulic acid glucoside. A peak that accumulates 70 fold is feruloyl malate (FIG. 7). *Arabidopsis* mutants with defective AT1G52760 lysophospholipase/thioesterase expression (esterase; green line) also have less lignin oligomers than wild-type plants (red line) (FIG. 8). The figure shows regions in the chromatogram that are rich in small lignin oligomers. Chromatograms of the thioesterase mutant have lower peak heights compared to the wild-type. Structures of some oligolignols that are reduced in the thioesterase mutant are shown. These data are being studied further to try to deduce the exact role of AT1G52760 mutants in lignin biosynthesis and new lines of investigation are being pursued to the same end.

Protein Complex Purification

In order to determine whether the AT1G52760 lysophospholipase interacted directly with lignin biosynthesis genes, the lysophospholipase was used as a bait to trap any interacting protein complexes using a tandem affinity purification system. Evaluation of the proteins co-purifying with the lysophospholipase by GC-MS revealed several potential lignin biosynthesis enzymes (data not shown). This suggests that the lysophosholipase influences lignin by some direct mechanism modulating lignin biosynthesis.

BLAST Searches for Orthologues in Other Species

Evaluation of AT1G52760 orthologues using BLAST searches of gene sequence data revealed several highly homologous sequences from *Populus trichocarpa, Vitis vinifera, Glycine max, Medicago truncatula* and *Oryza sativa*, suggesting that the role of AT52760 is widely conserved in the plant kingdom (FIG. 7).

TABLE 1

Cell wall and lignin amount and composition.

|  | Wild-type Control for Mx12_7 | Mx12_7 | Difference Mx12_7/WT | Wild-type Control for Gb9 | Gb9 | Difference Gb9/WT |
|---|---|---|---|---|---|---|
| CWR/dry weight (%) | 82.9 (1.4) | 79.0 (3.3) | — | 79.8 (2.8) | 72.9 (1.1)* | −9% |
| ABSL lignin/CWR (%) | 16.2 (1.0) | 13.4 (0.5)* | −17% | 17.6 (0.5) | 11.7 (0.6)*** | −33% |
| cellulose/CWR (%) | 45.0 (2.7) | 42.2 (3.5) | — | 59.7 (3.5) | 43.5 (1.1)** | −27% |
| H units/CWR (μmol/g) | 0.7 (0.1) | 2.6 (0.4)** | +270% | 0.4 (0.1) | 8.2 (0.6)*** | +1900% |
| G units/CWR (μmol/g) | 67.4 (5) | 41.1 (4.1)*** | −39% | 59.3 (4.5) | 12.0 (1.4)* | −80% |
| S units/CWR (μmol/g) | 20.7 (2.7) | 15.3 (2.2) | — | 31.4 (2.2) | 10.4 (1.3)*** | −67% |

TABLE 1-continued

Cell wall and lignin amount and composition.

|  | Wild-type Control for Mx12_7 | Mx12_7 | Difference Mx12_7/WT | Wild-type Control for Gb9 | Gb9 | Difference Gb9/WT |
|---|---|---|---|---|---|---|
| H + G + S/CWR (µmol/g) | 88.7 (7.6) | 59.0 (6.3)** | −33% | 91.1 (6.4) | 30.6 (3.2)*** | −66% |
| H units/lignin (µmol/g) | 5.0 (0.9) | 22.3 (3.8)** | +350% | 2.1 (0.4) | 71.2 (14.7)*** | +3300% |
| G units/lignin (µmol/g) | 467.9 (35) | 352.4 (35.3)* | −25% | 342.3 (36.2) | 104.8 (12.3)*** | −69% |
| S units/lignin (µmol/g) | 143.5 (18.8) | 131.2 (18.5) | — | 181.2 (19.4) | 90.7 (10.8)** | −50% |
| H + G + S/lignin (µmol/g) | 616.5 (53.1) | 505.9 (53.8) | — | 525.6 (54.6) | 266.7 (28.3)** | −49% |
| % H | 0.9 (0.2) | 4.4 (0.6)*** | +390% | 0.4 (0.1) | 27.1 (1.2)*** | +6700% |
| % G | 76.4 (1.1) | 70.0 (1.6)** | −8% | 65.0 (1) | 39.1 (0.8)*** | −40% |
| % S | 22.7 (1.2) | 25.6 (1.3) | — | 34.5 (1) | 33.8 (0.7) | — |
| S/G | 0.30 (0.02) | 0.37 (0.03)* | +23% | 0.53 (0.02) | 0.86 (0.02)*** | +62% |

ABSL lignin: lignin determined via the acetyl bromide soluble lignin (ABSL) protocol.
Lignin composition was determined via thioacidolysis.
Numbers between brackets are standard deviations.
*$0.01 < p < 0.05$;
**$0.001 < p < 0.01$;
***$p < 0.001$.
CWR: cell wall residue.

REFERENCES

1. Vanholme, R., Van Acker, R., Boerjan, W. (2010) Potential of Arabidopsis systems biology to advance the biofuel field. Trends Biotechnol. 28, 11, 543-547.
2. Berthet, S., Demont-Caulet, N., Pollet, B., Bidzinski, P., Cezard, L., Le Bris, P., Borrega, N., Herve, J., Blondet, E., Balzergue, S., Lapierre, C., & Jouanin, L. Disruption of LACCASE4 and 17 Results in Tissue-Specific Alterations to Lignification of Arabidopsis thaliana Stems. Plant Cell DOI 10.1105/tpc.110.082792 (2011).
3. C. Lapierre, G. Pilate, B. Pollet, I. Mila, J. C. Leplé, L. Jouanin, H. Kim and J. Ralph. (2004) Signatures of cinnamyl alcohol dehydrogenase deficiency in poplar lignins. C. Lapierre, G. Pilate, B. Pollet, I. Mila, J. C. Leplé, L. Jouanin, H. Kim and J. Ralph. Phytochemistry, 65(3), 313-321.
4. J. Ralph, H. Kim, F. Lu, J. H. Grabber, W. Boerjan, J.-C. Leplé, J. Berrio Sierra, M. Mir Derikvand, L. Jouanin and C. Lapierre. (2008) Identification of the structure and origin of a thioacidolysis marker compound for ferulic acid incorporation into angiosperm lignins (and an indicator for cinnamoyl-CoA reductase deficiency). The Plant Journal, 53(2), 368-379.
5. H. Kim, J. Ralph, F. Lu, S. A. Ralph, A.-M. Boudet, J. J. MacKay, R. R. Sederoff, T. Ito, S. Kawai, H. Ohashi and T. Higuchi. (2003) NMR Analysis of Lignins in CAD-deficient Plants. Part 1. Incorporation of hydroxycinnamaldehydes and hydroxybenzaldehydes into lignins. Organic and Biomolecular Chemistry, 1, 268-281.
6. Brown, D. M., Zeef, L. A., Ellis, J., Goodacre, R., & Turner S. R. Identification of Novel Genes in Arabidopsis Involved in Secondary Cell Wall Formation Using Expression Profiling and Reverse Genetics. Plant Cell 17:8, 2281-2295 (2005).
7. Manfield, I. W., Jen, C. H., Pinney, J. W., Michalopoulos, I., Bradford, J. R., Gilmartin, P. M., & Westhead, D. R. Arabidopsis Co-Expression Tool (ACT): Web Server Tools for Microarray-Based Gene Expression Analysis. Nucleic Acids Res. 34: suppl 2, W504-W509 (2006).
8. Srinivasasainagendra, V., Page, G. P., Mehta, T., Coulibaly, I., & Loraine, A. E. CressExpress: A Tool for Large-Scale Mining of Expression Data from Arabidopsis. Plant Physiol. 147:3, 1004-1016 (2008).
9. Hatfield, R. D., Grabber, J., Ralph, J., & Brei, K. Using the Acetyl Bromide Assay to Determine Lignin Concentrations in Herbaceous Plants: Some Cautionary Notes. J. Agric. Food Chem. 47:2, 628-632 (1999).
10. Gomez, L. D., Whitehead, C., Barakate, A., Halpin, C., & McQueen-Mason, S. J. (2010) Automated Saccharification Assay for Determination of Digestibility in Plant Materials. Biotechnol. Biofuels. 3:23.
11. Gao, W., Li, H. Y., Xiao, S., Chye, M. L. (2010) Acyl-CoA-binding protein 2 binds lysophospholipase 2 and lysoPC to promote tolerance to cadmium-induced oxidative stress in transgenic Arabidopsis. Plant J. 62, 989-1003.
12. Lusser, M., Paris, C., Plan, D. and Rodriguez-Cerezo, E. (2011) New plant breeding techniques: State-of-the-art and prospects for commercial development. JRC Scientific and Technical Reports. EUR 24760 EN-2011. doi: 10.2791/54.

The invention claimed is:

1. A genetically modified plant exhibiting reduced expression in comparison to a wild-type plant of one or more lysophospholipase 2 gene(s) having at least 95% sequence identity to or homology with SEQ ID NO: 1,
wherein the genetically modified plant comprises reduced lignin and/or reduced lignin composition than that found in the wild-type plant, and
wherein the plant is a species or hybrid selected from the group consisting of the *Saccharum*, *Zea*, *Triticum*, *Secale*, *Hordeum*, *Glycine*, *Oryza*, *Sorghum*, *Lolium*, *Vitis*, *Medicago*, *Eucalyptus*, *Populus*, and *Panicum* genera.

2. A genetically modified plant exhibiting reduced expression, function and/or activity in comparison to a wild-type plant of one or more lysophospholipase gene(s), the one or more lysophospholipase gene(s) selected from the group consisting of:
(i) a gene encoded by SEQ ID NO: 1;
(ii) a gene having at least about 95% sequence identity or homology with SEQ ID NO: 1;
(iii) a gene encoded by any of SEQ ID NOS: 3, 5, 7, 9, 11, or 15; and
(iv) a gene having at least about 95% sequence identity or homology with SEQ ID NOS: 3, 5, 7, 9, 11, or 15;
wherein said genetically modified plant comprises reduced lignin and/or reduced lignin composition in comparison to that found in the wild-type plant.

3. A genetically modified plant exhibiting reduced expression, function and/or activity in comparison to a wild-type plant of one or more lysophospholipase enzyme(s), the lysophospholipase enzyme(s) selected from the group consisting of:
(i) the peptide of SEQ ID NO: 2;
(ii) an esterase/lipophospholipase enzyme having at least about 95% sequence homology/identity with SEQ ID NO: 2;
(iii) an esterase/lipophospholipase enzyme encoded by a sequence corresponding to SEQ ID NO: 4, 6, 8, 10, 12, or 16; and
(iv) an esterase/lipophospholipase enzyme encoded by a polynucleotide having at least about 95% sequence homology/identity with any of SEQ ID NOs: 4, 6, 8, 10, 12, or 16;
wherein said genetically modified plant comprises reduced lignin and/or reduced lignin composition in comparison to that found in the wild-type plant.

4. A method of accessing and/or processing carbohydrate polymer(s) from plant matter, the method comprising:
utilizing a genetically modified plant that exhibits reduced expression in comparison to wild-type pant thereof of one or more lysophospholipase 2 gene(s) having at least 95% sequence identity to or homology with SEQ ID NO: 1 or stems, leaves, and/or roots from the genetically modified plant as the pint matter to assess and/or process carbohydrate polymers therefrom,
wherein the genetically modified plant has reduced a lignin composition in comparison to the wild-type plant thereof, and
wherein the plant is a species or hybrid selected from the group consisting of the *Saccharum*, *Zea*, *Triticum*, *Secale*, *Hordeum*, *Glycine*, *Oryza*, *Sorghum*, *Lolium*, *Vitis*, *Medicago*, *Eucalyptus*, *Populus*, and *Panicum* genera.

5. A method of producing a biofuel, the method comprising:
producing a biofuel with a fermentation process utilizing a genetically modified plant that exhibits reduced expression, function, and/or activity of one or more lysophospholipase gene(s) in comparison to a wild-type plant, the one or more lysophospholipase gene(s) selected from the group consisting of:
(i) a gene ene Encoded by SEQ ID NO: 1;
(ii) a gene having at least about 95% sequence identity or homology with SEQ ID NO: 1;
(iii) a gene encoded by any of SEQ ID NOs: 3, 5, 7, 9, 11, or 15; and
(iv) a gene having at least about 95% sequence identity or homology with SEQ ID NO: 3, 5, 7, 9, 11, or 15;
wherein the genetically modified plant has reduced lignin and/or reduced lignin composition in comparison to that found in the wild-type plant.

6. The method of claim 5, wherein the biofuel is a bioethanol.

7. A method of reducing the lignin content of a plant, the method comprising:
genetically modifying the plant to reduce expression, function and/or activity in comparison to a wild-type plant of one or more lysophospholipase 2 gene(s) having at least 95% sequence identity to or homology with SEQ ID NO: 1.

* * * * *

UNITED STATES PATENT AND TRADEMARK OFFICE
CERTIFICATE OF CORRECTION

PATENT NO. : 9,834,776 B2  
APPLICATION NO. : 14/399901  
DATED : December 5, 2017  
INVENTOR(S) : Wout Antoon Corneel Boerjan et al.

Page 1 of 1

It is certified that error appears in the above-identified patent and that said Letters Patent is hereby corrected as shown below:

In the Specification

| | | | |
|---|---|---|---|
| | Column 23, | Line 14, | change "200 bp-1 kb of" to --200 bp-1kb of-- |
| | Column 24, | Line 16, | change "AT1 G52760 was" to --AT1G52760 was-- |

In the Claims

| | | | |
|---|---|---|---|
| Claim 4, | Column 56, | Line 22, | change "wild-type pant thereof" to --wild-type plant thereof-- |
| Claim 4, | Column 56, | Line 26, | change "as the pint matter" to --as the plant matter-- |
| Claim 5, | Column 56, | Line 45, | change "gene ene Encoded by" to --gene encoded by-- |

Signed and Sealed this  
Twenty-second Day of May, 2018

Andrei Iancu  
*Director of the United States Patent and Trademark Office*

SEQUENCE LISTING

<160> NUMBER OF SEQ ID NOS: 18

<210> SEQ ID NO 1
<211> LENGTH: 1419
<212> TYPE: DNA
<213> ORGANISM: Arabidopsis sp.

<400> SEQUENCE: 1
ctttatcacc accaaaaacc aaaattcact gccaaaaaaa acacatcaaa acgatgccgt    60

| | |
|---|---|
| cggaagcgga gagctcagcg aattcagctc cggcaactcc gccaccacca ccgaatttct | 120 |
| ggggaaccat gccggaggaa gagtactaca cttcacaagg agtacgtaac agcaaatcat | 180 |
| acttcgaaac accaaacggc aagctcttca ctcagagctt cttaccatta gatggtgaaa | 240 |
| tcaaaggcac tgtgtacatg tctcatggat acggatccga tacaagctgg atgtttcaga | 300 |
| agatctgtat gagtttctct agttggggtt acgctgtttt cgccgccgat cttctcggtc | 360 |
| acggccgttc cgatggtatc cgctgctaca tgggttcgtt tacttcgttc ctctgttttg | 420 |
| ataagataaa ttttccatct ttgtgtaatt gataagataa tttacgatct ttaggtgatt | 480 |
| aaagattgga ttttatggt tattaggtga tatggagaaa gttgcagcaa catcattggc | 540 |
| tttcttcaag catgttcgtt gtagtgatcc atataaggat cttccggctt ttctgtttgg | 600 |
| tgaatcgatg ggaggtcttg tgacgctttt gatgtatttt caatcggaac ctgagacttg | 660 |
| gaccggtttg atgttttcgg ctcctctctt tgttatccct gaggatatga aaccaagcaa | 720 |
| ggctcatctt tttgcttatg gtctcctctt tggtttggct gatacgtggg ctgcaatgcc | 780 |
| ggataataag atggttggga aggctatcaa ggaccctgaa aagcttaaga tcatcgcttc | 840 |
| taacccgcaa aggtactatt aaacttcttg gaagcaaaca tagtataaag cttgagactt | 900 |
| tactttggaa gctataaaag tttggatttt gcattgtaga tatacaggga agcctagagt | 960 |
| gggaacaatg agagagttac tgaggaagac tcaatacgtt caggagaatt tcgggaaagt | 1020 |
| tactattccg gtgtttacgg cgcacgggac agccggatgga gtaacatgtc ctacatcttc | 1080 |
| gaagctacta tacgaaaaag cgtcaagcgc tgataaaacg ttgaagatct atgaagggat | 1140 |
| gtatcactcg ctgattcaag gagagcctga cgagaacgct gagatagtct tgaaggatat | 1200 |
| gagagagtgg atcgatgaga aggttaagaa gtatggatct aaaaccgctt gaacaaagct | 1260 |
| acatttgtgt tacaagaact tgaagagaaa tgtatattga tgttatgatc cgtatcgtcg | 1320 |
| atttgacttg ttttgttgtc tgttgtaatc caagaacatg aattttctga tgtaagaact | 1380 |
| tataatatca tggattacag aaatcctttt atcatttct | 1419 |

<210> SEQ ID NO 2
<211> LENGTH: 332
<212> TYPE: PRT
<213> ORGANISM: Arabidopsis sp.

<400> SEQUENCE: 2

Met Pro Ser Glu Ala Glu Ser Ser Ala Asn Ser Ala Pro Ala Thr Pro
1               5                   10                  15

Pro Pro Pro Pro Asn Phe Trp Gly Thr Met Pro Glu Glu Glu Tyr Tyr
            20                  25                  30

Thr Ser Gln Gly Val Arg Asn Ser Lys Ser Tyr Phe Glu Thr Pro Asn
        35                  40                  45

Gly Lys Leu Phe Thr Gln Ser Phe Leu Pro Leu Asp Gly Glu Ile Lys
    50                  55                  60

Gly Thr Val Tyr Met Ser His Gly Tyr Gly Ser Asp Thr Ser Trp Met
65                  70                  75                  80

Phe Gln Lys Ile Cys Met Ser Phe Ser Ser Trp Gly Tyr Ala Val Phe
                85                  90                  95

Ala Ala Asp Leu Leu Gly His Gly Arg Ser Asp Gly Ile Arg Cys Tyr
            100                 105                 110

Met Gly Asp Met Glu Lys Val Ala Ala Thr Ser Leu Ala Phe Phe Lys
        115                 120                 125

His Val Arg Cys Ser Asp Pro Tyr Lys Asp Leu Pro Ala Phe Leu Phe

```
                130              135              140
Gly Glu Ser Met Gly Gly Leu Val Thr Leu Leu Met Tyr Phe Gln Ser
145                 150                 155                 160

Glu Pro Glu Thr Trp Thr Gly Leu Met Phe Ser Ala Pro Leu Phe Val
                165                 170                 175

Ile Pro Glu Asp Met Lys Pro Ser Lys Ala His Leu Phe Ala Tyr Gly
            180                 185                 190

Leu Leu Phe Gly Leu Ala Asp Thr Trp Ala Ala Met Pro Asp Asn Lys
        195                 200                 205

Met Val Gly Lys Ala Ile Lys Asp Pro Glu Lys Leu Lys Ile Ile Ala
    210                 215                 220

Ser Asn Pro Gln Arg Tyr Thr Gly Lys Pro Arg Val Gly Thr Met Arg
225                 230                 235                 240

Glu Leu Leu Arg Lys Thr Gln Tyr Val Gln Glu Asn Phe Gly Lys Val
                245                 250                 255

Thr Ile Pro Val Phe Thr Ala His Gly Thr Ala Asp Gly Val Thr Cys
            260                 265                 270

Pro Thr Ser Ser Lys Leu Leu Tyr Glu Lys Ala Ser Ser Ala Asp Lys
        275                 280                 285

Thr Leu Lys Ile Tyr Glu Gly Met Tyr His Ser Leu Ile Gln Gly Glu
    290                 295                 300

Pro Asp Glu Asn Ala Glu Ile Val Leu Lys Asp Met Arg Glu Trp Ile
305                 310                 315                 320

Asp Glu Lys Val Lys Lys Tyr Gly Ser Lys Thr Ala
                325                 330

<210> SEQ ID NO 3
<211> LENGTH: 1316
<212> TYPE: DNA
<213> ORGANISM: Populus sp.

<400> SEQUENCE: 3
tcctccctcc cgcaaccagt tttaaaaaaa gttgaaacac cattatccaa ctccgaaacg      60
ccacccacct actccctgta aaaaccccct accgttttct ctgtttaaaa gtcaaccatc     120
caagccttac gataaccgta acgagacgtg accatgccat ccgaagcgca gcagcccgaa     180
gcgccaccca acttctgggg cgacatgccg gaggaggagt actatgcatc gcaaggagtg     240
accaataccc agtcacactt tgaaacgccg aatgggaagg tcttcacgca gggttttctc     300
ccgttggata aaaaggtcaa agccacggtg tatatgaccc acggctacgg atctgatact     360
ggctggctgt tcagaagatt tgcatcaac  tttgctacct ggggttatgc tgttttttgct     420 gctgatcttc ttgggcatgg cagatcagac ggtttacgct gctacatggg cgacatggag     480
aaaattgctg cagcgtccgt atcgttcttc aagcatgtgc gctacagcga gccatacaag     540
aacttgcccg ccttcttatt tggcgagtca atgggcggac tagcaacgat gctgatgtat     600
ttccaatcag aacctgacac gtggacgggc gtgattttct cggccccact tttcgtcata     660
ccggaaccaa tgaaacctag taaggcacac ctattcatgt atggcctgct ctttggattt     720
gctgacacgt gggcggccat gccagacaac aaaatggtag gtaaagcgat aaaggaccca     780
gagaaactca agatcatagc atccaacccc agaagataca caggcaagcc tagggtgggt     840
accatgagag aaattgccag agtctgccaa tacatacagg acaatttctc caaggttacg     900
gtgccgtttt tgactgtcca cgggaccgcc gatggggtga catgcccaac atcatcacag     960
ttgttgtatg agaaagcctc gagtgaggat aagagcttga agatgtacga gggcatgtac    1020
```

```
cattctttga tacaaggcga gcctgacgaa aatgcaagtc ttgtcttgaa ggatatgaga    1080
gagtggatcg atgagagggt tgagaggtat gggtctacaa agagtgatga ttgaaatcat    1140
atatgaagaa aaatggtgg tttttttct ggaaagtga agcttggtcc atagtctctt      1200
gatgggatta gggcaaaacg aatgccaatg taattgaata ttttgaact aacgaagtca    1260 gctattgctt ctctcgattt aatttataaa aaaaatgttt gaaacttta atttc          1316
```

<210> SEQ ID NO 4
<211> LENGTH: 326
<212> TYPE: PRT
<213> ORGANISM: Populus sp.

<400> SEQUENCE: 4

```
Met Pro Ser Glu Ala Gln Gln Pro Glu Ala Pro Asn Phe Trp Gly
1               5                   10                  15

Asp Met Pro Glu Glu Tyr Tyr Ala Ser Gln Gly Val Thr Asn Thr
            20                  25                  30

Gln Ser His Phe Glu Thr Pro Asn Gly Lys Val Phe Thr Gln Gly Phe
        35                  40                  45

Leu Pro Leu Asp Lys Lys Val Lys Ala Thr Val Tyr Met Thr His Gly
50                  55                  60

Tyr Gly Ser Asp Thr Gly Trp Leu Phe Gln Lys Ile Cys Ile Asn Phe
65                  70                  75                  80

Ala Thr Trp Gly Tyr Ala Val Phe Ala Ala Asp Leu Leu Gly His Gly
                85                  90                  95

Arg Ser Asp Gly Leu Arg Cys Tyr Met Gly Asp Met Glu Lys Ile Ala
            100                 105                 110

Ala Ala Ser Val Ser Phe Phe Lys His Val Arg Tyr Ser Glu Pro Tyr
        115                 120                 125

Lys Asn Leu Pro Ala Phe Leu Phe Gly Glu Ser Met Gly Gly Leu Ala
    130                 135                 140

Thr Met Leu Met Tyr Phe Gln Ser Glu Pro Asp Thr Trp Thr Gly Val
145                 150                 155                 160

Ile Phe Ser Ala Pro Leu Phe Val Ile Pro Glu Pro Met Lys Pro Ser
                165                 170                 175

Lys Ala His Leu Phe Met Tyr Gly Leu Leu Phe Gly Phe Ala Asp Thr
            180                 185                 190

Trp Ala Ala Met Pro Asp Asn Lys Met Val Gly Lys Ala Ile Lys Asp
        195                 200                 205

Pro Glu Lys Leu Lys Ile Ile Ala Ser Asn Pro Arg Arg Tyr Thr Gly
    210                 215                 220

Lys Pro Arg Val Gly Thr Met Arg Glu Ile Ala Arg Val Cys Gln Tyr
225                 230                 235                 240

Ile Gln Asp Asn Phe Ser Lys Val Thr Val Pro Phe Leu Thr Val His
                245                 250                 255

Gly Thr Ala Asp Gly Val Thr Cys Pro Thr Ser Ser Gln Leu Leu Tyr
            260                 265                 270

Glu Lys Ala Ser Ser Glu Asp Lys Ser Leu Lys Met Tyr Glu Gly Met
        275                 280                 285

Tyr His Ser Leu Ile Gln Gly Glu Pro Asp Glu Asn Ala Ser Leu Val
    290                 295                 300

Leu Lys Asp Met Arg Glu Trp Ile Asp Glu Arg Val Glu Arg Tyr Gly
305                 310                 315                 320
```

Ser Thr Lys Ser Asp Asp
            325

<210> SEQ ID NO 5
<211> LENGTH: 981
<212> TYPE: DNA
<213> ORGANISM: Populus sp.

<400> SEQUENCE: 5

| | |
|---|---:|
| atgtcatccg aaacgcagca acccgaaacg cctcccaact tctggggcga catgccggag | 60 |
| gaggagtact atgcgtcaca aggagtgacc actacccaat catacttcga dacgccaaat | 120 |
| gggaagctct tcacgcaagg ttttctcccg ttggataaaa aagtcaaagc cacggtatat | 180 |
| atgacccacg gctatggatc tgatactggc tggttgttcc agaagatttg catcagcttt | 240 |
| gctaactggg gttatgctgt ttttgccgct gatcttcttg acatggcag atcagacggt | 300 |
| atacgttgct acatgggtga catggacaag attgctgcca cttccctgtc attcttcaag | 360 |
| cacgagcgct tcagcgaacc atacaagggc ttaccagcct tcttatttgg tgaatcaatg | 420 |
| ggtggactca caacaatgct aatgtacttc caatcagaac ctaacatgtg dacgggcttg | 480 |
| attttctcgg cgccactttt tgtcatacca gaagcgatga accaagcaa ggtacaccta | 540 |
| ttcatgtatg gcctgctctt tggattggct gatacgtggg cagccatgcc agacaacaaa | 600 |
| atggtaggca aagcgatcaa ggacccagag aagctcaaga tcatagcatc caaccctagg | 660 |
| agatacacag gcaagcctag ggtgggaacc atgagggaaa ttgctaggat gtgccaatac | 720 |
| atacaggaca atttctccaa ggttacagcg ccgttcttga cagtccacgg cacggctgat | 780 |
| ggggtgacat gccctacatc atcacagttg ttgtttgaga aagcctctag tgaggacaag | 840 |
| agcttgaaga tgtacgaggg catgtaccat tctttgatac aaggtgagcc cgatgagaat | 900 |
| gctaatcttg ttttgaagga tatgagaggg tggattgacg agagggttga gaggtatggg | 960 |
| tccaaaaaaa gcgatgactg a | 981 |

<210> SEQ ID NO 6
<211> LENGTH: 326
<212> TYPE: PRT
<213> ORGANISM: Populus sp.

<400> SEQUENCE: 6

Met Ser Ser Glu Thr Gln Gln Pro Glu Thr Pro Asn Phe Trp Gly
1               5                  10                 15

Asp Met Pro Glu Glu Glu Tyr Tyr Ala Ser Gln Gly Val Thr Thr Thr
                20                  25                 30

Gln Ser Tyr Phe Glu Thr Pro Asn Gly Lys Leu Phe Thr Gln Gly Phe
         35                 40                  45

Leu Pro Leu Asp Lys Lys Val Lys Ala Thr Val Tyr Met Thr His Gly
     50                 55                  60

Tyr Gly Ser Asp Thr Gly Trp Leu Phe Gln Lys Ile Cys Ile Ser Phe
65              70                  75                  80

Ala Asn Trp Gly Tyr Ala Val Phe Ala Ala Asp Leu Leu His Gly
                85                  90                  95

Arg Ser Asp Gly Ile Arg Cys Tyr Met Gly Asp Met Asp Lys Ile Ala
                100                 105                110

Ala Thr Ser Leu Ser Phe Phe Lys His Glu Arg Phe Ser Glu Pro Tyr
         115                120                 125

Lys Gly Leu Pro Ala Phe Leu Phe Gly Glu Ser Met Gly Gly Leu Thr
     130                135                 140

Thr Met Leu Met Tyr Phe Gln Ser Glu Pro Asn Met Trp Thr Gly Leu
145                 150                 155                 160

Ile Phe Ser Ala Pro Leu Phe Val Ile Pro Glu Ala Met Lys Pro Ser
                165                 170                 175

Lys Val His Leu Phe Met Tyr Gly Leu Leu Phe Gly Leu Ala Asp Thr
            180                 185                 190

Trp Ala Ala Met Pro Asp Asn Lys Met Val Gly Lys Ala Ile Lys Asp
        195                 200                 205

Pro Glu Lys Leu Lys Ile Ile Ala Ser Asn Pro Arg Arg Tyr Thr Gly
210                 215                 220

Lys Pro Arg Val Gly Thr Met Arg Glu Ile Ala Arg Met Cys Gln Tyr
225                 230                 235                 240

Ile Gln Asp Asn Phe Ser Lys Val Thr Ala Pro Phe Leu Thr Val His
                245                 250                 255

Gly Thr Ala Asp Gly Val Thr Cys Pro Thr Ser Ser Gln Leu Leu Phe
            260                 265                 270

Glu Lys Ala Ser Ser Glu Asp Lys Ser Leu Lys Met Tyr Glu Gly Met
        275                 280                 285

Tyr His Ser Leu Ile Gln Gly Glu Pro Asp Glu Asn Ala Asn Leu Val
290                 295                 300

Leu Lys Asp Met Arg Gly Trp Ile Asp Glu Arg Val Glu Arg Tyr Gly
305                 310                 315                 320

Ser Lys Lys Ser Asp Asp
                325

<210> SEQ ID NO 7
<211> LENGTH: 966
<212> TYPE: DNA
<213> ORGANISM: Vitis vinifera

<400> SEQUENCE: 7
atgtcgtcgg aatccgaaat tcggccaac ttctggggcg atatgccgga ggaggagtac      60
tatgcctccc aagggtgcg caacaccaaa tcatayttcg acaccccaa cggcaagctc     120 ttcacccaga gtttcctacc cttggatctc cctgtcaagg cttccgtcta catgacccac     180
ggctacggct ccgacaccgg ctggctcttc cagaagattt gcattaacta cgccacctgg     240 gctacgcag tcttcgccgc cgacatcctc ggccacggcc gctccgacgg yatccgctgc     300
tacctcggcg acatggagaa ggtcgccgcc acctcccttt cyttcttcaa gagcgtycgc     360
accagcgaat cctaccgyga cctccctgct ttcctcttcg gcgagtccat gggtggggct     420
accaccatgc tcgtgtactt ccaatcggag ccggagctgt ggacaggcct gatcttctca     480
gccccacttt tcgtgatgcc ggagaacatg aagccgtcga aggtgaggct attcctgtac     540
ggacttctgt ttgggatggc tgacacgtgg gcgacgatgc cggacaacaa gatggtgggg     600
aaggcgatca ggatccgga gaagctgaag gtcatagcgt cgaatccacg gcggtacacg     660
ggtccgccga gggtggggac gatgagggag ctggctaggg tgtgccagta catacaggat     720
aatttctcga argtgackgc gccgttcttg acggtgcacg gacggcrga tggggtgacg     780 tgtccgacgt cgtcgaagct gctgtacgag aaggcttcga gtgaggacaa agcattgaag     840
ttgtatgagg ggatgtacca ttcttttgata cagggagagc ctgatgagaa tkccaatctg     900
gtgttgaagg atatgaggga atggattgat gagagggttg agagatacgg accctccaaa     960
tcctag                                                                966

<210> SEQ ID NO 8
<211> LENGTH: 321
<212> TYPE: PRT
<213> ORGANISM: Vitis vinifera
<220> FEATURE:
<221> NAME/KEY: misc_feature
<222> LOCATION: (298)..(298)
<223> OTHER INFORMATION: Xaa can be any naturally occurring amino acid

<400> SEQUENCE: 8

```
Met Ser Ser Glu Ser Glu Ile Ser Ala Asn Phe Trp Gly Asp Met Pro
 1               5                  10                  15

Glu Glu Glu Tyr Tyr Ala Ser Gln Gly Val Arg Asn Thr Lys Ser Tyr
            20                  25                  30

Phe Asp Thr Pro Asn Gly Lys Leu Phe Thr Gln Ser Phe Leu Pro Leu
        35                  40                  45

Asp Leu Pro Val Lys Ala Ser Val Tyr Met Thr His Gly Tyr Gly Ser
    50                  55                  60

Asp Thr Gly Trp Leu Phe Gln Lys Ile Cys Ile Asn Tyr Ala Thr Trp
65                  70                  75                  80

Gly Tyr Ala Val Phe Ala Ala Asp Ile Leu Gly His Gly Arg Ser Asp
                85                  90                  95

Gly Ile Arg Cys Tyr Leu Gly Asp Met Glu Lys Val Ala Ala Thr Ser
            100                 105                 110

Leu Ser Phe Phe Lys Ser Val Arg Thr Ser Glu Ser Tyr Arg Asp Leu
        115                 120                 125

Pro Ala Phe Leu Phe Gly Glu Ser Met Gly Gly Ala Thr Thr Met Leu
    130                 135                 140

Val Tyr Phe Gln Ser Glu Pro Glu Leu Trp Thr Gly Leu Ile Phe Ser
145                 150                 155                 160

Ala Pro Leu Phe Val Met Pro Glu Asn Met Lys Pro Ser Lys Val Arg
                165                 170                 175

Leu Phe Leu Tyr Gly Leu Leu Phe Gly Met Ala Asp Thr Trp Ala Thr
            180                 185                 190

Met Pro Asp Asn Lys Met Val Gly Lys Ala Ile Lys Asp Pro Glu Lys
        195                 200                 205

Leu Lys Val Ile Ala Ser Asn Pro Arg Arg Tyr Thr Gly Pro Pro Arg
    210                 215                 220

Val Gly Thr Met Arg Glu Leu Ala Arg Val Cys Gln Tyr Ile Gln Asp
225                 230                 235                 240

Asn Phe Ser Lys Val Thr Ala Pro Phe Leu Thr Val His Gly Thr Ala
                245                 250                 255

Asp Gly Val Thr Cys Pro Thr Ser Ser Lys Leu Leu Tyr Glu Lys Ala
            260                 265                 270

Ser Ser Glu Asp Lys Ala Leu Lys Leu Tyr Glu Gly Met Tyr His Ser
        275                 280                 285

Leu Ile Gln Gly Glu Pro Asp Glu Asn Xaa Asn Leu Val Leu Lys Asp
    290                 295                 300

Met Arg Glu Trp Ile Asp Glu Arg Val Glu Arg Tyr Gly Pro Ser Lys
305                 310                 315                 320

Ser
```

<210> SEQ ID NO 9
<211> LENGTH: 1232
<212> TYPE: DNA
<213> ORGANISM: Medicago truncatula

<400> SEQUENCE: 9

```
aatctctaat tatccatcct cacccgtttc catcgctgaa acaacaacgc caatggcaac      60
gcagcaggaa tcagagattc ccccaaattt ctggggtcac accccgaag aagaatacta     120
cacctcccaa ggagttcgca ataccaaatc acacttcgaa acacccaacg gcaaaatctt    180
cacacagtcc tttctcccac tcaacgctga atcaaagct accgtttaca tgactcacgg     240
ttacggctcc gacaccggct ggctcttcca aaaaatctgc atcacctacg ccacctgggg    300
ttacgccgtc ttcaccgctg atctcttagg tcacggccgt tccgatggcc tccgttgcta    360
cctcggggac atggacaaaa tcgccgccac ctcactttca ttttcctcc acgtccgccg     420
ttctcctccc tacaaccacc tcccagcgtt tctcttcggt gagtcaatgg gtggtttagc    480
tacattgctg atgtatttcc aatcagaacc cgacacgtgg acgggtttaa tattctcagc    540
gccgctttc gtaatccccg aggatatgaa accgagtaag attcatttgt tgtgtacgg      600
tcttttgttt ggtttggctg acacgtgggc agcgatgcct gataacaaaa tggtcggaaa    660
agcaattagg gatccaaata agttgaagat tattgcttct aatccaagga ggtatacggg    720
cccacctaga gtagggacca tgagggaact tcttagagtc actcaatatg tgcaagataa    780
tttctgcaat gtaacggtgc cgtttcttac ggcacatggt actgctgatg gtgtcacgtg    840
cccttcttct tctaagctgt tgtatgagaa agctgaatct aaggataaga ctttgaagct    900
ttatgagggg atgtatcatt ctttgattca agggagcct gatgagtctg ctaatcttgt     960
gttaagggat atgagggagt ggattgatga gagggttcgt aggtatggac ctaataatga   1020
taattctcaa tgaaaaacaa gggtggctgt tgtgtttttt tttcatacaa tttttagttt   1080
ggaattacct ggtctcgata atcaagattt gattgaggac tattgttatg actatattga   1140
aatttttatg actatatgaa cgaactgtga tgttgttata tggtgtgctt cgtttagatc   1200
cttctataca taacaatatg atcttacggt tc                                 1232
```

<210> SEQ ID NO 10
<211> LENGTH: 326
<212> TYPE: PRT
<213> ORGANISM: Medicago truncatula

<400> SEQUENCE: 10

```
Met Ala Thr Gln Gln Glu Ser Glu Ile Pro Pro Asn Phe Trp Gly His
1               5                   10                  15

Thr Pro Glu Glu Tyr Tyr Thr Ser Gln Gly Val Arg Asn Thr Lys
            20                  25                  30

Ser His Phe Glu Thr Pro Asn Gly Lys Ile Phe Thr Gln Ser Phe Leu
        35                  40                  45

Pro Leu Asn Ala Glu Ile Lys Ala Thr Val Tyr Met Thr His Gly Tyr
    50                  55                  60

Gly Ser Asp Thr Gly Trp Leu Phe Gln Lys Ile Cys Ile Thr Tyr Ala
65                  70                  75                  80

Thr Trp Gly Tyr Ala Val Phe Thr Ala Asp Leu Leu Gly His Gly Arg
                85                  90                  95

Ser Asp Gly Leu Arg Cys Tyr Leu Gly Asp Met Asp Lys Ile Ala Ala
            100                 105                 110

Thr Ser Leu Ser Phe Phe Leu His Val Arg Arg Ser Pro Pro Tyr Asn
        115                 120                 125

His Leu Pro Ala Phe Leu Phe Gly Glu Ser Met Gly Gly Leu Ala Thr
    130                 135                 140
```

```
Leu Leu Met Tyr Phe Gln Ser Glu Pro Asp Thr Trp Thr Gly Leu Ile
145                 150                 155                 160

Phe Ser Ala Pro Leu Phe Val Ile Pro Glu Asp Met Lys Pro Ser Lys
            165                 170                 175

Ile His Leu Phe Val Tyr Gly Leu Leu Phe Gly Leu Ala Asp Thr Trp
        180                 185                 190

Ala Ala Met Pro Asp Asn Lys Met Val Gly Lys Ala Ile Arg Asp Pro
    195                 200                 205

Asn Lys Leu Lys Ile Ile Ala Ser Asn Pro Arg Arg Tyr Thr Gly Pro
210                 215                 220

Pro Arg Val Gly Thr Met Arg Glu Leu Leu Arg Val Thr Gln Tyr Val
225                 230                 235                 240

Gln Asp Asn Phe Cys Asn Val Thr Val Pro Phe Leu Thr Ala His Gly
                245                 250                 255

Thr Ala Asp Gly Val Thr Cys Pro Ser Ser Lys Leu Leu Tyr Glu
            260                 265                 270

Lys Ala Glu Ser Lys Asp Lys Thr Leu Lys Leu Tyr Glu Gly Met Tyr
        275                 280                 285

His Ser Leu Ile Gln Gly Glu Pro Asp Glu Ser Ala Asn Leu Val Leu
    290                 295                 300

Arg Asp Met Arg Glu Trp Ile Asp Glu Arg Val Arg Arg Tyr Gly Pro
305                 310                 315                 320

Asn Asn Asp Asn Ser Gln
                325

<210> SEQ ID NO 11
<211> LENGTH: 1295
<212> TYPE: DNA
<213> ORGANISM: Medicago truncatula

<400> SEQUENCE: 11
acccaatcgc aatggcaccg gaatcagagg ctccccctaa cttctggggc cacaccccgg      60
aagaagaata ctacacctcc caaggcgttc gcaacaccaa gtcccacttc gaaaccccca     120
acggcaaaat cttcacccag tccttcctcc ctctcaacct ccaacccac caagtcaaag     180 ccaccgtctt tatgacccac ggctacggct ccgacaccgg ctggctcttc cagaaaatct     240
gcatcaactt cgccacctgg ggctacgccg tcttcgccgc cgacctcctc ggccacggcc     300
gctccgacgg tctccagtgc tacctcggcg acatggacaa aatcgccgcc acctccctct     360
ccttcttcct ccacgtccgc aatagccacc cctacaaaaa cctcccggca ttcctcttcg     420
gcgagtccat gggaggactc gccacgctcc tcatgtactt caaatcggaa ccggacacgt     480
ggacgggcct gatgttctcc gcgccactct tcgtgattcc cgaggacatg aaacccagca     540
gggtacattt gttcatgtac ggtctcttgt tcggtctcgc cgacacgtgg gcggccatgc     600
cggataacaa aatggtcgga aaggccatca gggatcccga agttgaag gtcatagcgt     660 cgaacccgag gcgctacacg ggcccaccca gggtggggac catgcgggag ctgcttaggg     720
tgacacagta tgtacaggat aatttctcca aggtaacgac gccgttttc actgctcacg     780 gaacttctga cggcgttacc tgcccttcct cgtccaagct gctgtatgag aagggttcca     840
gtgaggataa gacgttgaag ctctacgatg gaatgtatca ctctttgatt cagggagagc     900
ccgatgagtc tgcgaatctc gtgttggggg acatgagaga gtggattgat gagagggttc     960
gacggtatgg acctaacaaa aattcccagt gaaacaaacc attactaaat tcctattttg    1020
```

```
gttccacatt gcatattttg tgtctatcaa aactttatta aagttgttat gtgaagacgg    1080
aagagtatcc ttcttctatc atatttggat ttcaatcaaa aatgacattt aatcaatcca    1140
gttatcggtt tcgatgcatg attaacttta gtcctaatct ctcaggatat agtagtaata    1200
aattcctcat agtccaggtt tcaaagttta tattagtcga aaattatgt gaaacctaag     1260 gaagtttaca aaatcagat agagagagat atttc                                1295
```

<210> SEQ ID NO 12
<211> LENGTH: 326
<212> TYPE: PRT
<213> ORGANISM: Medicago truncatula

<400> SEQUENCE: 12

```
Met Ala Pro Glu Ser Glu Ala Pro Pro Asn Phe Trp Gly His Thr Pro
1               5                   10                  15

Glu Glu Glu Tyr Tyr Thr Ser Gln Gly Val Arg Asn Thr Lys Ser His
                20                  25                  30

Phe Glu Thr Pro Asn Gly Lys Ile Phe Thr Gln Ser Phe Leu Pro Leu
            35                  40                  45

Asn Leu Gln Pro His Gln Val Lys Ala Thr Val Phe Met Thr His Gly
        50                  55                  60

Tyr Gly Ser Asp Thr Gly Trp Leu Phe Gln Lys Ile Cys Ile Asn Phe
65                  70                  75                  80

Ala Thr Trp Gly Tyr Ala Val Phe Ala Ala Asp Leu Leu Gly His Gly
                85                  90                  95

Arg Ser Asp Gly Leu Gln Cys Tyr Leu Gly Asp Met Asp Lys Ile Ala
            100                 105                 110

Ala Thr Ser Leu Ser Phe Phe Leu His Val Arg Asn Ser His Pro Tyr
        115                 120                 125

Lys Asn Leu Pro Ala Phe Leu Phe Gly Glu Ser Met Gly Gly Leu Ala
130                 135                 140

Thr Leu Leu Met Tyr Phe Lys Ser Glu Pro Asp Thr Trp Thr Gly Leu
145                 150                 155                 160

Met Phe Ser Ala Pro Leu Phe Val Ile Pro Glu Asp Met Lys Pro Ser
                165                 170                 175

Arg Val His Leu Phe Met Tyr Gly Leu Leu Phe Gly Leu Ala Asp Thr
            180                 185                 190

Trp Ala Ala Met Pro Asp Asn Lys Met Val Gly Lys Ala Ile Arg Asp
        195                 200                 205

Pro Glu Lys Leu Lys Val Ile Ala Ser Asn Pro Arg Arg Tyr Thr Gly
    210                 215                 220

Pro Pro Arg Val Gly Thr Met Arg Glu Leu Leu Arg Val Thr Gln Tyr
225                 230                 235                 240

Val Gln Asp Asn Phe Ser Lys Val Thr Thr Pro Phe Phe Thr Ala His
                245                 250                 255

Gly Thr Ser Asp Gly Val Thr Cys Pro Ser Ser Ser Lys Leu Leu Tyr
            260                 265                 270

Glu Lys Gly Ser Ser Glu Asp Lys Thr Leu Lys Leu Tyr Asp Gly Met
        275                 280                 285

Tyr His Ser Leu Ile Gln Gly Glu Pro Asp Glu Ser Ala Asn Leu Val
    290                 295                 300

Leu Gly Asp Met Arg Glu Trp Ile Asp Glu Arg Val Arg Arg Tyr Gly
305                 310                 315                 320

Pro Asn Lys Asn Ser Gln
```

<210> SEQ ID NO 13
<211> LENGTH: 1000
<212> TYPE: DNA
<213> ORGANISM: Oryza sativa

<400> SEQUENCE: 13

```
atggcgccgc caccgccgcc accgacggcg acgaagtact tctggggcga ctccccggag      60
cccgacgagt actacgcctc gctgggtctc cgccacgccg aggcctactt ccagtccccc     120
tgcggccgcc tcttcacgca ctcgttccac ccgctctccg ccgccagcga cggcgacgtc     180
aagggcgtcg tcttcatgag ccacggctac ggctccgact cctcgtggat gttccagaac     240
atcgccatca gctacgcgcg gtggggtac gccgtcttct cgccgacct gctcggacac      300
ggccgctccg acggcgtccg cggctacctc ggcgacacgg aggccgtcgc gagggcggcg     360
ctctccttct cctctccgt gcggcggagc ggcgcctacg cctccctccc ggcgttcctc     420
ttcggcgagt ccatgggcgg cgccaccacc ctgctcgcct acctccgctc cccgcccgac     480
gccgggtggg cggggatcat cctgtcggcg ccgctgctcg tcttccccga cgacatgtac     540
ccgtcccgcg tgcggctctt cctgtacggc ctcctcttcg tctagccga cacatgggcg     600
gtgatgccgg acaagaggat ggtggggaga tcgatccgcg acccggcgaa gctgagggtg     660
atcgcgtcca acccgcggct gtaccgcggc tcgccgcggg tggggacgat gcgggagctc     720
gcacgcgtga cggcgctgct gcgggagagc ttcggggagg tggcggcgcc gttcctggtg     780
gtgcacggca ccgacgacgg ggtgacctcg ccggaggggt ccaggatgct gtacgagcgc     840
gcggcgagcg aggacaagag cctcatcctc tacgacggga tgtaccactc gctcatccag     900
ggggagtccg acgagaaccg cgaccgcgtg ctcgccgaca tgcgcgcctg gatcgacgag     960
cgcgtccgcc gctacggcgc cggcgccggc gccgcggcgg                          1000
```

<210> SEQ ID NO 14
<211> LENGTH: 343
<212> TYPE: PRT
<213> ORGANISM: Oryza sativa

<400> SEQUENCE: 14

```
Met Ala Pro Pro Pro Pro Pro Thr Ala Thr Lys Tyr Phe Trp Gly
1               5                   10                  15

Asp Ser Pro Glu Pro Asp Glu Tyr Tyr Ala Ser Leu Gly Leu Arg His
                20                  25                  30

Ala Glu Ala Tyr Phe Gln Ser Pro Cys Gly Arg Leu Phe Thr His Ser
            35                  40                  45

Phe His Pro Leu Ser Ala Ala Ser Asp Gly Asp Val Lys Gly Val Val
        50                  55                  60

Phe Met Ser His Gly Tyr Gly Ser Asp Ser Ser Trp Met Phe Gln Asn
65                  70                  75                  80

Ile Ala Ile Ser Tyr Ala Arg Trp Gly Tyr Ala Val Phe Cys Ala Asp
                85                  90                  95

Leu Leu Gly His Gly Arg Ser Asp Gly Val Arg Gly Tyr Leu Gly Asp
            100                 105                 110

Thr Glu Ala Val Ala Arg Ala Ala Leu Ser Phe Phe Leu Ser Val Arg
        115                 120                 125

Arg Ser Gly Ala Tyr Ala Ser Leu Pro Ala Phe Leu Phe Gly Glu Ser
    130                 135                 140
```

Met Gly Gly Ala Thr Thr Leu Leu Ala Tyr Leu Arg Ser Pro Pro Asp
145                 150                 155                 160

Ala Gly Trp Ala Gly Ile Ile Leu Ser Ala Pro Leu Leu Val Phe Pro
                165                 170                 175

Asp Asp Met Tyr Pro Ser Arg Val Arg Leu Phe Leu Tyr Gly Leu Leu
            180                 185                 190

Phe Gly Leu Ala Asp Thr Trp Ala Val Met Pro Asp Lys Arg Met Val
        195                 200                 205

Gly Arg Ser Ile Arg Asp Pro Ala Lys Leu Arg Val Ile Ala Ser Asn
    210                 215                 220

Pro Arg Leu Tyr Arg Gly Ser Pro Arg Val Gly Thr Met Arg Glu Leu
225                 230                 235                 240

Ala Arg Val Thr Ala Leu Leu Arg Glu Ser Phe Gly Glu Val Ala Ala
                245                 250                 255

Pro Phe Leu Val Val His Gly Thr Asp Asp Gly Val Thr Ser Pro Glu
            260                 265                 270

Gly Ser Arg Met Leu Tyr Glu Arg Ala Ala Ser Glu Asp Lys Ser Leu
        275                 280                 285

Ile Leu Tyr Asp Gly Met Tyr His Ser Leu Ile Gln Gly Glu Ser Asp
    290                 295                 300

Glu Asn Arg Asp Arg Val Leu Ala Asp Met Arg Ala Trp Ile Asp Glu
305                 310                 315                 320

Arg Val Arg Arg Tyr Gly Ala Gly Ala Gly Ala Ala Ala Ala Asp Gly
                325                 330                 335

His Ala Glu Ala Pro Ala Ala
            340

<210> SEQ ID NO 15
<211> LENGTH: 933
<212> TYPE: DNA
<213> ORGANISM: Eucalyptus grandis

<400> SEQUENCE: 15
ttctgggggc acatgccgga ggatgagtac tacgcgtcgc aaggggtgcg caactcccag        60
tcctacttcg agaccccaaa cggcaagctc ttcacgcaga gcttccttcc cttggatcag       120
gaagtcaagg cctcggtcta catgacccac ggctacggat ccgacaccgg ctggctcttc       180
cagaagatct gcatcaactt cgccacctgg ggctacgccg tcttcgccgc cgatctcctc       240
ggccacggcc gctccgacgg cctccgttgc tacatgggtg acatggagaa gatcgctgcc       300
acctccgtat cgttcttcac ccacgtccgc aagagcgagc cctacaagga cctgccggcc       360
ttcctgttcg gcgagtccat gggcggggcg acgacaatgc tgatgtactt ccaatccgag       420
cccgacgcat ggacgggatt gatcttctcg gcgccgctct tcgtgatccc ggagaacatg       480
aagcccagca aggtacggct gttcctctac ggcatgctct cggggtcgc cgacacgtgg       540 gcgagcatgc cggacaacaa gatggtgggg aaggccatca aggaccccga aagctcaag       600 atcatcgcgt cgaacccgcg gaggtacacg ggcaagccga gggtcggcac gatgagggag       660
atcgcccggg tgtgccagta catacaggac aacttcgcca gggtgagcgc cccgttcctg       720
acggtccacg gacgtcgga cggggtcacg tgccccacct cgtcgcagct cctgtacgag       780
aaggcgtcca gctcggacaa gaccctgaag ctgtacgacg ggatgtacca ctcgctgatc       840 caggggagc ccgacgagaa cgccgaccgg gtgttgggcg acatgaggga gtggatcgac       900
gagcgggtcg cgaggtacgg gccgaagatc gcc                                    933

<210> SEQ ID NO 16
<211> LENGTH: 311
<212> TYPE: PRT
<213> ORGANISM: Eucalyptus sp

<400> SEQUENCE: 16

```
Phe Trp Gly His Met Pro Glu Asp Glu Tyr Tyr Ala Ser Gln Gly Val
1               5                   10                  15

Arg Asn Ser Gln Ser Tyr Phe Glu Thr Pro Asn Gly Lys Leu Phe Thr
            20                  25                  30

Gln Ser Phe Leu Pro Leu Asp Gln Glu Val Lys Ala Ser Val Tyr Met
        35                  40                  45

Thr His Gly Tyr Gly Ser Asp Thr Gly Trp Leu Phe Gln Lys Ile Cys
    50                  55                  60

Ile Asn Phe Ala Thr Trp Gly Tyr Ala Val Phe Ala Ala Asp Leu Leu
65                  70                  75                  80

Gly His Gly Arg Ser Asp Gly Leu Arg Cys Tyr Met Gly Asp Met Glu
                85                  90                  95

Lys Ile Ala Ala Thr Ser Val Ser Phe Phe Thr His Val Arg Lys Ser
            100                 105                 110

Glu Pro Tyr Lys Asp Leu Pro Ala Phe Leu Phe Gly Glu Ser Met Gly
        115                 120                 125

Gly Ala Thr Thr Met Leu Met Tyr Phe Gln Ser Glu Pro Asp Ala Trp
    130                 135                 140

Thr Gly Leu Ile Phe Ser Ala Pro Leu Phe Val Ile Pro Glu Asn Met
145                 150                 155                 160

Lys Pro Ser Lys Val Arg Leu Phe Leu Tyr Gly Met Leu Phe Gly Val
                165                 170                 175

Ala Asp Thr Trp Ala Ser Met Pro Asp Asn Lys Met Val Gly Lys Ala
            180                 185                 190

Ile Lys Asp Pro Glu Lys Leu Lys Ile Ile Ala Ser Asn Pro Arg Arg
        195                 200                 205

Tyr Thr Gly Lys Pro Arg Val Gly Thr Met Arg Glu Ile Ala Arg Val
    210                 215                 220

Cys Gln Tyr Ile Gln Asp Asn Phe Ala Arg Val Ser Ala Pro Phe Leu
225                 230                 235                 240

Thr Val His Gly Thr Ser Asp Gly Val Thr Cys Pro Thr Ser Ser Gln
                245                 250                 255

Leu Leu Tyr Glu Lys Ala Ser Ser Ser Asp Lys Thr Leu Lys Leu Tyr
            260                 265                 270

Asp Gly Met Tyr His Ser Leu Ile Gln Gly Glu Pro Asp Glu Asn Ala
        275                 280                 285

Asp Arg Val Leu Gly Asp Met Arg Glu Trp Ile Asp Glu Arg Val Ala
    290                 295                 300

Arg Tyr Gly Pro Lys Ile Ala
305                 310
```

<210> SEQ ID NO 17
<211> LENGTH: 933
<212> TYPE: DNA
<213> ORGANISM: Panicum virgatum

<400> SEQUENCE: 17

```
accaagtact tctggggcga caccccgag cccgacgagt actacgccgc gcaggggctc      60
cggcacgccg agtcctactt ccagtcccct cacggccgcc tcttcaccca cgccttccac     120
```

```
ccgctcgccg gcgacgtcaa gggcgtcgtc ttcatgaccc acggctacgg ttccgactcc      180
tcgtggctct tccagaccgc cgccatcagc tacgcgcgct gggggtacgc cgtcttctgc      240
gccgacctcc tcggccacgg ccgctccgac ggcctccgcg gtacgtcgg cgacatggag       300 gccgccgccg cggcgtccct cgcttttctt ctctccgtgc gcgccagcgc ggcgtacgcc      360
gcgctcccgg cgttcctgtt cggcgagtcc atgggcggcg ccgccacgct gctcatgtac      420
ctccgctccc cgccgtccgc cgcgctggacg gggctcgtgc tctcggcgcc gctcctcgtc      480
atccccgacg gcatgtaccc gtcccgcctc cgcctcttcc tgtacggcct cctcttcggc      540
ctcgccgaca cctgggccgt gctcccggac aagaggatgg tggggaaggc gatcaaggac      600
cccgacaagc tgcggcttat cgcgtccaac ccgctcggct accgcggcgc cgcgcgggtg      660
ggcacgatgc gggagctggt ccgcgtgacg gatctgctgc gggagagcct cggggaggtg      720
gcggcgccgt tcctcgccgt gcacgggacg gacgacggcg tgacctcgcc ggaggggtcc      780
aggatgctgt acgagcgcgc gagcagcgag gacaaggagc tcatcctgta cgaggggatg      840
taccactcgc tcatccaggg ggagcccgac gagaaccgcg accgcgtgct cgccgacatg      900
cgcaggtgga tcgacgagcg cgtgcgccgc tac                                  933
```

<210> SEQ ID NO 18
<211> LENGTH: 311
<212> TYPE: PRT
<213> ORGANISM: Panicum virgatum

<400> SEQUENCE: 18

```
Thr Lys Tyr Phe Trp Gly Asp Thr Pro Glu Pro Asp Glu Tyr Tyr Ala
1               5                   10                  15

Ala Gln Gly Leu Arg His Ala Glu Ser Tyr Phe Gln Ser Pro His Gly
            20                  25                  30

Arg Leu Phe Thr His Ala Phe His Pro Leu Ala Gly Asp Val Lys Gly
        35                  40                  45

Val Val Phe Met Thr His Gly Tyr Gly Ser Asp Ser Ser Trp Leu Phe
    50                  55                  60

Gln Thr Ala Ala Ile Ser Tyr Ala Arg Trp Gly Tyr Ala Val Phe Cys
65                  70                  75                  80

Ala Asp Leu Leu Gly His Gly Arg Ser Asp Gly Leu Arg Gly Tyr Val
                85                  90                  95

Gly Asp Met Glu Ala Ala Ala Ala Ser Leu Ala Phe Phe Leu Ser
            100                 105                 110

Val Arg Ala Ser Ala Ala Tyr Ala Ala Leu Pro Ala Phe Leu Phe Gly
        115                 120                 125

Glu Ser Met Gly Gly Ala Ala Thr Leu Leu Met Tyr Leu Arg Ser Pro
    130                 135                 140

Pro Ser Ala Arg Trp Thr Gly Leu Val Leu Ser Ala Pro Leu Leu Val
145                 150                 155                 160

Ile Pro Asp Gly Met Tyr Pro Ser Arg Leu Arg Leu Phe Leu Tyr Gly
                165                 170                 175

Leu Leu Phe Gly Leu Ala Asp Thr Trp Ala Val Leu Pro Asp Lys Arg
            180                 185                 190

Met Val Gly Lys Ala Ile Lys Asp Pro Asp Lys Leu Arg Leu Ile Ala
        195                 200                 205

Ser Asn Pro Leu Gly Tyr Arg Gly Ala Pro Arg Val Gly Thr Met Arg
    210                 215                 220
```

-continued

```
Glu Leu Val Arg Val Thr Asp Leu Leu Arg Glu Ser Leu Gly Glu Val
225                 230                 235                 240

Ala Ala Pro Phe Leu Ala Val His Gly Thr Asp Asp Gly Val Thr Ser
            245                 250                 255

Pro Glu Gly Ser Arg Met Leu Tyr Glu Arg Ala Ser Ser Glu Asp Lys
            260                 265                 270

Glu Leu Ile Leu Tyr Glu Gly Met Tyr His Ser Leu Ile Gln Gly Glu
        275                 280                 285

Pro Asp Glu Asn Arg Asp Arg Val Leu Ala Asp Met Arg Arg Trp Ile
        290                 295                 300

Asp Glu Arg Val Arg Arg Tyr
305                 310
```